(12) United States Patent
Sosnowski et al.

(10) Patent No.: US 7,582,421 B2
(45) Date of Patent: *Sep. 1, 2009

(54) METHODS FOR DETERMINATION OF SINGLE NUCLEIC ACID POLYMORPHISMS USING A BIOELECTRONIC MICROCHIP

(75) Inventors: Ronald G. Sosnowski, Coronado, CA (US); Michael I. Nerenberg, La Jolla, CA (US); David M. Canter, San Diego, CA (US); Ray R. Radtkey, San Diego, CA (US); Ling Wang, San Diego, CA (US); James P. O'Connell, Solana Beach, CA (US)

(73) Assignee: Nanogen, Inc., San Diego, CA (US)

( * ) Notice: Subject to any disclaimer, the term of this patent is extended or adjusted under 35 U.S.C. 154(b) by 943 days.

This patent is subject to a terminal disclaimer.

(21) Appl. No.: 10/245,206

(22) Filed: Sep. 16, 2002

(65) Prior Publication Data

US 2003/0073122 A1 Apr. 17, 2003

Related U.S. Application Data

(63) Continuation of application No. 09/291,129, filed on Apr. 12, 1999, now Pat. No. 6,468,742.

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl. ................ 435/6; 435/91.1; 435/91.2; 536/23.1; 536/24.3; 536/24.33; 536/25.3; 536/25.32

(58) Field of Classification Search .............. 435/6, 435/91.1, 91.2, 183, 283.1, 287.1, 287.2; 436/94; 536/23.1, 24.3, 24.33, 25.3; 422/50, 422/68.1

See application file for complete search history.

(56) References Cited

U.S. PATENT DOCUMENTS 3,950,738 A    4/1976   Hayashi et al.

(Continued)

FOREIGN PATENT DOCUMENTS

EP    0228075 A2    7/1987

(Continued)

OTHER PUBLICATIONS

AAAC, "Hemochromotosis More Prevalent Than Previously Believed", Clinical Laboratory News, 1999, vol. 25, No. 2.

(Continued)

*Primary Examiner*—Frank W Lu

(57) ABSTRACT

This application includes methods for detecting single nucleotide polymorphisms (SNPs) in a sample using an electronically addressable microchip having a plurality of test sites. A sample nucleic acid is electronically biased, concentrated at, and immobilized to a test site on the microchip. A mixture comprising a first labeled probe and a second labeled probe is electronically hybridized to the sample nucleic acid to form first or second hybridized complexes. The first labeled probe is perfectly complementary to the first sample nucleic acid and the second labeled probe is complementary to the sample nucleic acid and contains a nucleotide that forms a mismatch with the nucleotide at the site of the polymorphism. The first or second hybridized complexes are detected by determining a signal intensity of the label of the first or second probe.

8 Claims, 12 Drawing Sheets

U.S. PATENT DOCUMENTS

| | | | |
|---|---|---|---|
| 3,995,190 | A | 11/1976 | Salgo |
| 4,283,773 | A | 8/1981 | Daughton et al. |
| 4,563,419 | A | 1/1986 | Ranki et al. |
| 4,580,895 | A | 4/1986 | Patel |
| 4,584,075 | A | 4/1986 | Goldstein et al. |
| 4,594,135 | A | 6/1986 | Goldstein |
| 4,731,325 | A | 3/1988 | Palva et al. |
| 4,751,177 | A | 6/1988 | Stabinsky |
| 4,787,963 | A | 11/1988 | MacConnell |
| 4,807,161 | A | 2/1989 | Comfort et al. |
| 4,816,418 | A | 3/1989 | Mack et al. |
| 4,822,566 | A | 4/1989 | Newman |
| 4,828,979 | A | 5/1989 | Klevan et al. |
| 4,883,750 | A | 11/1989 | Whiteley et al. |
| 4,908,112 | A | 3/1990 | Pace |
| 4,988,617 | A | 1/1991 | Landegren et al. |
| 5,030,557 | A | 7/1991 | Hogan et al. |
| 5,063,081 | A | 11/1991 | Cozzette et al. |
| 5,074,977 | A | 12/1991 | Cheung et al. |
| 5,075,077 | A | 12/1991 | Durley, III et al. |
| 5,096,669 | A | 3/1992 | Lauks et al. |
| 5,096,807 | A | 3/1992 | Leaback |
| 5,114,674 | A | 5/1992 | Stanbro et al. |
| 5,125,748 | A | 6/1992 | Bjornson |
| 5,126,022 | A | 6/1992 | Soane et al. |
| 5,143,854 | A | 9/1992 | Pirrung et al. |
| 5,164,319 | A | 11/1992 | Hafeman et al. |
| 5,166,063 | A | 11/1992 | Johnson |
| 5,200,051 | A | 4/1993 | Cozzette et al. |
| 5,202,231 | A | 4/1993 | Drmanac et al. |
| 5,219,726 | A | 6/1993 | Evans |
| 5,227,265 | A | 7/1993 | DeBoer et al. |
| 5,234,566 | A | 8/1993 | Osman et al. |
| 5,242,797 | A | 9/1993 | Hirschfeld |
| 5,304,487 | A | 4/1994 | Wilding et al. |
| 5,312,527 | A | 5/1994 | Mikkelsen et al. |
| 5,433,819 | A | 7/1995 | McMeen |
| 5,434,049 | A | 7/1995 | Okano et al. |
| 5,436,129 | A | 7/1995 | Stapleton |
| 5,445,525 | A | 8/1995 | Broadbent et al. |
| 5,445,934 | A | 8/1995 | Fodor et al. |
| 5,464,517 | A | 11/1995 | Hjerten et al. |
| 5,468,646 | A | 11/1995 | Mattingly et al. |
| 5,474,895 | A | 12/1995 | Ishii et al. |
| 5,516,641 | A | 5/1996 | Ullman et al. |
| 5,516,698 | A | 5/1996 | Begg et al. |
| 5,527,670 | A | 6/1996 | Stanley |
| 5,552,270 | A | 9/1996 | Khrapko et al. |
| 5,573,907 | A | 11/1996 | Carrino et al. |
| 5,593,838 | A | 1/1997 | Zanzucchi et al. |
| 5,602,240 | A | 2/1997 | DeMesmaeker et al. |
| 5,605,662 | A | 2/1997 | Heller et al. |
| 5,632,957 | A | 5/1997 | Heller et al. |
| 5,635,352 | A | 6/1997 | Urdea et al. |
| 5,653,939 | A | 8/1997 | Hollis et al. |
| 5,660,701 | A | 8/1997 | Grushka et al. |
| 5,681,751 | A | 10/1997 | Begg et al. |
| 5,750,015 | A | 5/1998 | Soane et al. |
| 5,766,960 | A | 6/1998 | Cornell et al. |
| 5,770,365 | A | 6/1998 | Lane et al. |
| 5,780,233 | A | 7/1998 | Guo et al. |
| 5,789,167 | A | 8/1998 | Konrad |
| 5,795,714 | A | 8/1998 | Przetaklewlcz et al. |
| 5,811,269 | A | 9/1998 | Nadeau et al. |
| 5,849,486 | A | 12/1998 | Heller et al. |
| 5,849,489 | A | 12/1998 | Heller et al. |
| 5,849,544 | A | 12/1998 | Harris et al. |
| 5,853,993 | A | 12/1998 | Dellinger et al. |
| 5,908,745 | A | 6/1999 | Mirzabekov et al. |
| 5,965,452 | A | 10/1999 | Kovacs |
| 6,013,166 | A | 1/2000 | Heller |
| 6,017,696 | A | 1/2000 | Heller |
| 6,048,690 | A | 4/2000 | Heller et al. |
| 6,051,380 | A | 4/2000 | Sosnowski et al. |
| 6,054,270 | A | 4/2000 | Southern |
| 6,068,818 | A | 5/2000 | Ackley et al. |
| 6,071,394 | A | 6/2000 | Cheng et al. |
| 6,099,803 | A | 8/2000 | Ackley et al. |
| 6,129,828 | A | 10/2000 | Sheldon, III et al. |
| 6,150,095 | A | 11/2000 | Southern et al. |
| 6,207,373 | B1 | 3/2001 | Sosnowski et al. |
| 6,306,348 | B1 | 10/2001 | Havens et al. |
| 6,309,602 | B1 | 10/2001 | Ackley et al. |
| 6,309,823 | B1 | 10/2001 | Cronin et al. |
| 6,403,367 | B1 | 6/2002 | Cheng et al. |
| 6,410,231 | B1 | 6/2002 | Arnold et al. |
| 6,451,526 | B1 | 9/2002 | Song et al. |
| 6,458,584 | B1 | 10/2002 | Mirzabekov et al. |
| 6,468,742 | B2 | 10/2002 | Nerenberg et al. |

FOREIGN PATENT DOCUMENTS

| | | |
|---|---|---|
| EP | 0320308 A2 | 6/1989 |
| EP | 0373203 A1 | 6/1990 |
| GB | 2156074 A | 10/1985 |
| GB | 2247889 A | 3/1992 |
| WO | WO 86/03782 A1 | 7/1986 |
| WO | WO 88/08528 A1 | 11/1988 |
| WO | WO 89/01159 A1 | 2/1989 |
| WO | WO 89/10977 A1 | 11/1989 |
| WO | WO 90/01564 A1 | 2/1990 |
| WO | WO 92/04470 A1 | 3/1992 |
| WO | WO 93/22678 A2 | 11/1993 |
| WO | WO 95/07363 A1 | 3/1995 |
| WO | WO 95/12808 A1 | 5/1995 |
| WO | WO 96/01836 A1 | 1/1996 |
| WO | WO 96/07917 A1 | 3/1996 |
| WO | WO 96/15271 A1 | 5/1996 |
| WO | WO 96/31622 A1 | 10/1996 |
| WO | WO 97/12030 A1 | 4/1997 |
| WO | WO 98/01758 A1 | 1/1998 |
| WO | WO 98/10273 A1 | 3/1998 |
| WO | WO 98/10277 A1 | 3/1998 |
| WO | WO 98/24544 A1 | 6/1998 |
| WO | WO 98/28444 A2 | 7/1998 |
| WO | WO 98/51819 A1 | 11/1998 |
| WO | WO 99/06593 A | 2/1999 |
| WO | WO 99/29711 A1 | 6/1999 |
| WO | WO 99/42558 A1 | 8/1999 |
| WO | WO 99/43853 A1 | 9/1999 |
| WO | WO 00/32744 A1 | 6/2000 |
| WO | WO 00/37163 A1 | 6/2000 |
| WO | WO 00/58522 A1 | 10/2000 |
| WO | WO 00/61803 A1 | 10/2000 |
| WO | WO 01/06496 A1 | 1/2001 |
| YU | 57087 A | 8/1990 |

OTHER PUBLICATIONS

Abrams et al., "Comprehensive Detection Of Single Base Changes In Human Genomic DNA Using Denaturing Gradient Gel Electrophoresis & GC Clamp", Genomics, Aug. 1990, 463-475, vol. 7, No. 4.

Anand et al., "Pulsed Field Electrophoresis", *Gel Electrophoresis of Nucleic Acids—A Practical Approach*, 1990, 101-123, Eds. D. Rickwood & B.D. Harnes (New York: IRL Press).

Anderson et al, "Quantitative Filter Hybridization", *Nucleic Acid Hybridization-A Practical Approach*, 1985, 73-111, Eds. B.D.Hames & S.J.Higgins (Washington, D.C.:IRL Press).

Bains, Setting A Sequence To Sequence A Sequence, Bio/Technology, 1992, 757-758, vol. 10.

Barinaga, "Will DNA Chip' Speed Genome Initiative?", Science, 1991, 1489, vol. 253.

Beattie et al, "Genosensor Technology", *The 1992 San Diego Conference: Genetic Recognition*, Nov. 1991, 1-5.

Beltz et al, "Isolation Of Multigene Families & Determination Of Homologies By Filter Hybridization Methods", Methods In Enzymology, 1983, 266-285, vol. 100.

Bertina, "Mutation In Blood Coagulation Factor V Associated With Resistance To Activated Protein C", Nature, 1994, 64-67, vol. 369.

Broude, N.E., et al. "Enhanced DNA Sequencing by Hybridization," Proc. Natl. Acad. Sci., 1994: 3072-76, vol. 91.

Brown et al, "Electrochemically Induced Adsorption Of Radio-Labelled DAN On Gold & HOPG Substrates For STM Investigations", Ultramicroscopy, 1991, 253-264, vol. 38.

Conner et al, "Detection Of Sickle Cell $\beta^3$—Globin Allele by Hybridization With Synthetic Oligonucleotides", Proc.Natl.Acad.Sci.USA, 1983, 278-282, vol. 80.

Day, "Electrophoresis For Genotyping: Microfilter Array Diagonal Gel Electrophoresis On Horizontal Polyacrylamide Gels, Hydrolink, Agarose", Analytical Biochemistry, 1994, 389-395, vol. 222.

Drmanac et al, "Sequencing Of Megabase Plus DNA By Hybridization: Theory of the Method", Genomics, 1989, 114-128, vol. 4.

Drmanac et al, "DNA Sequence Determination By Hybridization: A Strategy For Efficient Large Scale Sequencing", Science, 1993, 1649-1652, vol. 260.

Drobyshev et al., Sequence Analysis By Hybridization With Oligonucleotide Microchip: Identification of β-Thalassemia Mutations, Gene 1997, 45-52, 188.

Drobyshev et al, "Massive Parallel Analysis Of DNA-Hoeschst 33258 Binding Specificity with A Generic Oligodeoxyribonucleotide Microchip", Nucleic Acids Research, 1999, 4100-4105, vol. 27, No. 20.

Edman, C.F., et al. "Electric field directed nucleic acid hybridization on microchips." Nucleic Acids Research, 1997, 4907-14, vol. 25, No. 24.

Eggers et al, "Biochip Technology Development", BioChip Technology Development, Lincoln Laboratory Technical Report 901, Nov. 9, 1990.

Feder, "The Hemochromatosis Founder Mutation In HLA-H Disrupts β2 Microglobulin Interaction & Cell Surface Expression", J. Biological Chemistry, 1997, 14025-14028, vol. 272, No. 22.

Fiaccabrino et al., "Array of Individually Addressable Microelectrodes", Sensors & Actuators B, 1994, 675-677, vol. 18-19.

Fodor et al, "Multiplexed Biochemical Assays with Biological Chips", Nature, 1993, 555-556, vol. 364.

Fodor et al, "Light Directed, Spatially Addressable Parallel Chemical Synthesis", Science, 1992, 767-773, vol. 251.

Gills et al, "Single Nucleotide Polymorphic Discrimination By An Electronic Dot Blot Assay On Semiconductor Microchips", Nature Biotechnology, Apr. 1999, 365-370, vol. 17.

Gryaznov et al, "Enhancement of Selectivity In Recognition Of Nucleic Acids Via Chemical Autoligation", Nucleic Acids Research, 1994, 2366-2369, vol. 22, No. 12 (University Press).

Guschin et al., "Manual Manufacturing Of Oligonucleotide DNA, And Protein Microchips", Anal. Biochem., Aug. 1, 1997, 203-211, vol. 250, No. 2.

Holland, "Detection Of Specific Polymerase Chain Reaction Product By Utilizing The 5'3' Exonuclease Activity of Thermus Aquaticus DNA Polymerase", Proc.Natl.Acad.Sci.USA, 1991, 7276-7280, vol. 88.

Horejsi, Some Theoretical Aspects of Affinity Electrophoresis, Journal Of Chromatography, 1979, 1-13, vol. 178.

Horesji et al, "Determination Of Dissociation Constants Of Lectin Sugar Complexes By Means Of Affinity Electrophoresis", Biochimica at Biophysica Acta, 1977, 200-300, vol. 499.

Howell, "Dynamic Allele-Specific Hybridization: A New Method For Scoring Single Nucleotide Polymorphisms", Nature Biotechnology, 1999, 87, vol. 17.

Kakerow et al, "A Monolithic Sensor Array of Individually Addressable Microelectrodes", Sensors & Actuators A, 1994, 296-301, vol. 43.

Khrapko, "An Oligonucleotide Hybridization Approach to DNA Sequencing" FEBS, 1989, 118-122, vol. 256 (1&2).

Khrapko et al., "A Method For DNA Sequencing By Hybridization With Oligonucleotide Matrix", DNA Seq., 1991, 375, vol. 1, No. 6.

Kieleczawa, "DNA Sequencing By Primer Walking With Strings of Contiquous Hexamers", Science, 1992, 1787, vol. 258.

Kotler, "DNA Sequencing: Modular Primers Associated From A Library Of Hexamers Of Pentamers", Proc.Natl.Acad.Sci.USA, 1993, 4241-4245, vol. 90.

Landegren, Reading Bits of Genetic Information: Methods For Single Nucleotide Polymorphism Analysis, Genome Research, 1998, 769-776, vol. 8.

Maldonado-Rodrequez et al., "Hybridization of Glass-Tethered Oligonucleotide Probes to Target Strands Preannealed with Labeled Auxiliary Oligonucleotides", Mol. Biotechnol., 1999, 1-12, vol. 11, No. 1.

Maldonado-Rodrequez et al., "Mutation Detection By Stacking Hybridization On Genosensor Arrays", Mol. Biotechnol., 1999, 13-25, vol. 11, No. 1.

Mathews et al, "Analytical Strategies For The Use Of DNA Probes", Analytical Biochemistry, 1988, 1-25, vol. 169.

Meade et al, "Electron Transfer Through DNA: Site-Specific Modification of Duplex DNA With Ruthenium Donors & Acceptors", Angew. Chem. Int. Ed. Engl., 1995, 353-354, vol. 34, No. 3.

Newton, "Analysis of Any Point Mutation in DNA. The Amplification Refractory Mutation System (ARMS)", 1989, Nucleic Acids Research, 1989, 2503, vol. 17, No. 7.

Norberg, "Solvent Influence on Base Stacking", Biophysical Journal, 1998, 394-402, vol. 74.

Orita, "Detection Of Polymorphisms Of Human DNA By Gel Electrophoresis As Single Strand Conformation Polymorphisms", Proc.Natl.Acad.Sci.USA, 1989, 2776-2770, vol. 86.

Ornstein, "An Optimized Potential Function For The Calculation Of Nucleic Acid Interaction Energies. I. Base Stacking", Biopolymers, 1978, 2341-2360, vol. 17.

Palecek, "New Trends In Electrochemical Analysis of Nucleic Acids", Bioelectrochemistry & Bioenergetics, 1988, 179-194, vol. 20.

Parinov, "DNA Sequencing By Hybridization To Microchip Octa- and Decanucleotides Extended By Stacked Pentanucleotides", Nucleic Acids Research, 1996, 2998-3004, vol. 24, No. 15.

Paton, Heterogenelty Of The Amino Acid Sequences Of *Escherichica coli* Shiga-like Toxin Type-I Operons, Gene, 1995, 71-74, vol. 153.

Pieters, "Conformational & Thermodynamic Consequences Of The Introduction Of A Nick In Duplexed DNA Fragments: An NMR Study Augmented By Biochemical Experiments", Nucleic Acids Research, 1989, 4551, vol. 17, No. 12.

Ranki et al, "Sandwich Hybridization As A Convenient Method For The Detection Of Nucleic Acids In Crude Samples", Gene, 1983, 77-85, vol. 21.

Saiki, "An Amplification of Genomic DNA", *PCR Protocols: A Guide To Methods & Applications*, 1990, 13-20, (Academic Press, Inc.).

Sinden, "Introduction To The Structure, Properties & Reactions of DNA", *DNA Structure & Function*, 1994, Chapter 1, (Academic Press).

Sosnowski, "Rapid Determination of Single Base Mismatch Mutations In DNA Hybrids By Direct Electric Field Control", Proc.Natl. Acad.Sci.USA, 1997, 1119-1123, vol. 94.

Southern, "Analyzing & Comparing Nucleic Acid Sequences By Hybridization To Arrays Of Oligonucleotides: Evaluation Using Experimental Models", Genomics, 1992, 1008-1017, vol. 13.

Southern, "DNA Chips: Analysing Sequence By Hybridization To Oligonucleotides On A Large Scale", Trends In Genetics, Mar. 1996, 110-115, vol. 12, No. 3.

Strezoska, "DNA Sequencing By Hybridization: 100 Bases Read By A Non-Gel Based Method", Proc.Natl.Acad.Sci.USA, 1991, 10089-10093, vol. 88.

Syvanen et al, "Fast Quantification Of Nucleic Acid Hybrids By Affinity-Based Hybrid Collection", Nucleic Acids Research, 1986, 5037-5048, vol. 14, No. 12.

Syvanen et al, "Quantification Of Polymerase Chain Reaction Products By Affinity Based Hybrid Collection", Nucleic Acids Research, 1988, 11327-11338, vol. 16, No. 23.

Syvanen, "A Primer Guided Nucleotide Incorporation Assay In Genotyping Of Apolipoprotein E", Genomics, 1990, 684-692, vol. 8.

Tyagi, "Molecular Beacons: Probes That Fluoresce Upon Hybridization", Nature Biotechnology, 1996, 303, vol. 14.

Wallace et al, "Hybridization Of Synthetic Oligodexribonucleotides To Φx 174 DNA: The Effect Of Single Base Pair Mismatch", Nucleic Acids Research, 1979, 3543-3557, vol. 6.

Wang, Large Scale Identification, Mapping & Genotyping Of Single Nucleotide Polymorphisms In The Human Genome, Science, 1998, 1077, vol. 280.

Washizu, "Electrostatic Manipulation of Biological Objects", Journal of Electrostatics, 1990, 109-123, vol. 25.

Washizu et al, "Electrostatic Manipulation Of DNA In Microfabricated Structures", IEEE Transactions On Industry Applications, 1990, 1165-1172, vol. 26.

Wu, "Specificity Of The Nick-closing Activity Of Bateriophage T4 DNA Ligase", Gene, 1989, 245-254, vol. 76.

Yershov et al, "DNA Analysis & Diagnostics On Oligonucleotide Microchips", Proc.Natl.Acad.Sci.USA, May 1996, 4913-4918, vol. 93.

Affymetrix, Data Sheet, GeneChip® Human Genome Arrays, 2003, 1-4.

Scouten W.H. et al. "Enzyme or Protein Immobilization Techniques for Applications in Biosensor Design." Trends in Biotechnology, vol. 13, No. 5, May 1995, pp. 178-185.

Attachment for "genetic marker", http://bdid.com/termsg.htm, Oct. 13, 2006.

Iannuzzi, et al., "Two Frameshift Mutations In The Cystic Fibrosis Gene", Am J. Hum. Genet., 48:227-231, 1991.

FIG. 4
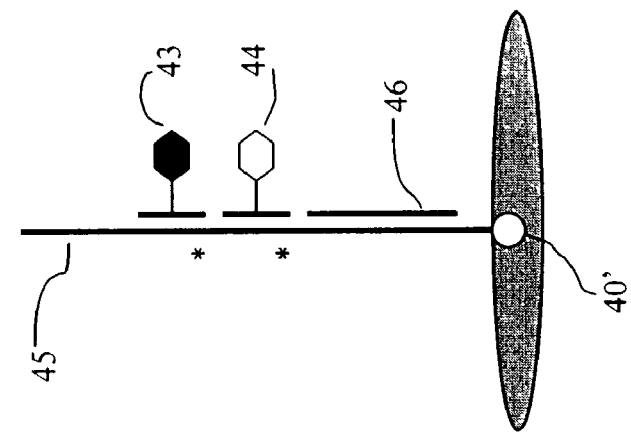
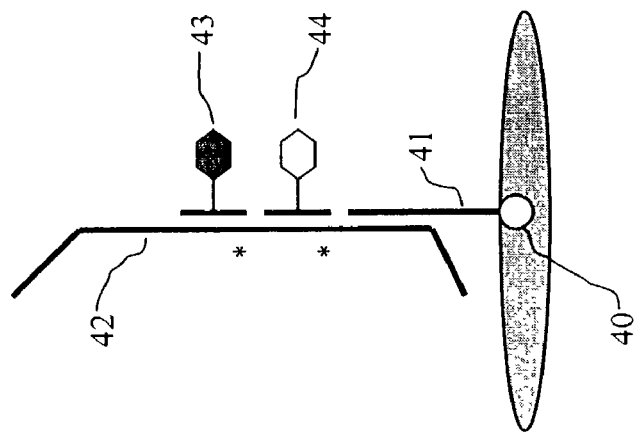

```
                            SEQUENCE LISTING

<160> NUMBER OF SEQ ID NOS: 17

<210> SEQ ID NO 1
<211> LENGTH: 20
<212> TYPE: DNA
<213> ORGANISM: human

<400> SEQUENCE: 1
tgttatcaca ctggtgctaa                                              20

<210> SEQ ID NO 2
<211> LENGTH: 20
<212> TYPE: DNA
<213> ORGANISM: human

<400> SEQUENCE: 2
actacagtga cgtggacatc                                              20

<210> SEQ ID NO 3
<211> LENGTH: 30
<212> TYPE: DNA
<213> ORGANISM: human

<400> SEQUENCE: 3
taatctgtaa gagcagatcc ctggacaggc                                   30

<210> SEQ ID NO 4
<211> LENGTH: 11
<212> TYPE: DNA
<213> ORGANISM: human

<400> SEQUENCE: 4
gaggaataca g                                                       11

<210> SEQ ID NO 5
<211> LENGTH: 11
<212> TYPE: DNA
<213> ORGANISM: human

<400> SEQUENCE: 5
aaggaataca g                                                       11

<210> SEQ ID NO 6
<211> LENGTH: 19
<212> TYPE: DNA
<213> ORGANISM: human

<400> SEQUENCE: 6
tgaaggataa gcagccaat                                               19

<210> SEQ ID NO 7
<211> LENGTH: 19
```

```
<212> TYPE: DNA
<213> ORGANISM: human

<400> SEQUENCE: 7
ctcctctcaa cccccaata                                          19

<210> SEQ ID NO 8
<211> LENGTH: 30
<212> TYPE: DNA
<213> ORGANISM: human

<400> SEQUENCE: 8
ggctgatcca ggcctgggtg ctccacctgg                              30

<210> SEQ ID NO 9
<211> LENGTH: 30
<212> TYPE: DNA
<213> ORGANISM: human

<400> SEQUENCE: 9
gggctgatcc aggcctgggt gctccacctg                              30

<210> SEQ ID NO 10
<211> LENGTH: 30
<212> TYPE: DNA
<213> ORGANISM: human

<400> SEQUENCE: 10
cacaatgagg ggctgatcca ggcctgggtg                              30

<210> SEQ ID NO 11
<211> LENGTH: 11
<212> TYPE: DNA
<213> ORGANISM: human

<400> SEQUENCE: 11
cacgtatatc t                                                  11

<210> SEQ ID NO 12
<211> LENGTH: 11
<212> TYPE: DNA
<213> ORGANISM: human

<400> SEQUENCE: 12
tacgtatatc t                                                  11

<210> SEQ ID NO 13
<211> LENGTH: 20
<212> TYPE: DNA
<213> ORGANISM: human

<400> SEQUENCE: 13
actacagtga cgtggacatc                                         20

<210> SEQ ID NO 14
<211> LENGTH: 20
<212> TYPE: DNA
<213> ORGANISM: human

<400> SEQUENCE: 14
tgttatcaca ctggtgctaa                                         20

<210> SEQ ID NO 15
```

```
<211> LENGTH: 30
<212> TYPE: DNA
<213> ORGANISM: human

<400> SEQUENCE: 15
ttacttcaag gacaaaatac ctgtattcct                                    30

<210> SEQ ID NO 16
<211> LENGTH: 11
<212> TYPE: DNA
<213> ORGANISM: human

<400> SEQUENCE: 16
cgcctgtcca g                                                        11

<210> SEQ ID NO 17
<211> LENGTH: 11
<212> TYPE: DNA
<213> ORGANISM: human

<400> SEQUENCE: 17
tgcctgtcca g                                                        11
```

METHODS FOR DETERMINATION OF SINGLE NUCLEIC ACID POLYMORPHISMS USING A BIOELECTRONIC MICROCHIP

RELATED APPLICATION INFORMATION

This is a continuation of Ser. No. 09/291,129, filed Apr. 12, 1999, now issued as U.S. Pat. No. 6,468,742, which is incorporated herein by reference as if fully set forth herein.

FIELD OF THE INVENTION

The methods of this invention relate to systems for genetic identification for disease states and other gene related afflictions. More particularly, the methods relate to systems for the detection of single nucleic acid polymorphisms in nucleic acid sequences for the identification of polymorphisms in viruses, and eukaryotic and prokaryotic genomes.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to that invention.

Molecular biology comprises a wide variety of techniques for the analysis of nucleic acid and protein sequences. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual*, 2 Ed., Cold spring Harbor Laboratory Press, Cold Spring Harbor, N.Y., 1989).

Most of these techniques involve carrying out numerous operations (e.g., pipetting, centrifugation, and electrophoresis) on a large number of samples. They are often complex and time consuming, and generally require a high degree of accuracy. Many a technique is limited in its application by a lack of sensitivity, specificity, or reproducibility.

For example, the complete process for carrying out a DNA hybridization analysis for a genetic or infectious disease is very involved. Broadly speaking, the complete process may be divided into a number of steps and sub-steps. In the case of genetic disease diagnosis, the first step involves obtaining the sample (e.g., saliva, blood or tissue). Depending on the type of sample, various pre-treatments would be carried out. The second step involves disrupting or lysing the cells which releases the crude DNA material along with other cellular constituents.

Generally, several sub-steps are necessary to remove cell debris and to further purify the DNA from the crude sample. At this point several options exist for further processing and analysis. One option involves denaturing the DNA and carrying out a direct hybridization analysis in one of many formats (dot blot, microbead, microplate, etc.). A second option, called Southern blot hybridization, involves cleaving the DNA with restriction enzymes, separating the DNA fragments on an electrophoretic gel, blotting the DNA to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out an amplification procedure such as the polymerase chain reaction (PCR) or the strand displacement amplification (SDA) method. These procedures amplify (increase) the number of target DNA sequences relative to non-target sequences. Amplification of target DNA helps to overcome problems related to complexity and sensitivity in genomic DNA analysis. After these sample preparation and DNA processing steps, the actual hybridization reaction is performed. Finally, detection and data analysis convert the hybridization event into an analytical result.

Nucleic acid hybridization analysis generally involves the detection of a very small number of specific target nucleic acids (DNA or RNA) with an excess of probe DNA, among a relatively large amount of complex non-target nucleic acids. A reduction in the complexity of the nucleic acid in a sample is helpful to the detection of low copy numbers (i.e. 10,000 to 100,000) of nucleic acid targets. DNA complexity reduction is achieved to some degree by amplification of target nucleic acid sequences. (See, M. A. Innis et al., *PCR Protocols: A Guide to Methods and Applications*, Academic Press, 1990, Spargo et al., 1996, *Molecular & Cellular Probes*, in regard to SDA amplification). This is because amplification of target nucleic acids results in an enormous number of target nucleic acid sequences relative to non-target sequences thereby improving the subsequent target hybridization step.

The actual hybridization reaction represents one of the most important and central steps in the whole process. The hybridization step involves placing the prepared DNA sample in contact with a specific reporter probe at set optimal conditions for hybridization to occur between the target DNA sequence and probe.

Hybridization may be performed in any one of a number of formats. For example, multiple sample nucleic acid hybridization analysis has been conducted in a variety of filter and solid support formats (See G. A. Beltz et al., in *Methods in Enzymology*, Vol. 100, Part B, R. Wu, L. Grossman, K. Moldave, Eds., Academic Press, New York, Chapter 19, pp. 266-308, 1985). One format, the so-called "dot blot" hybridization, involves the non-covalent attachment of target DNAs to a filter followed by the subsequent hybridization to a radio-isotope labeled probe(s). "Dot blot" hybridization gained wide-spread use over the past two decades during which time many versions were developed (see M. L. M. Anderson and B. D. Young, in *Nucleic Acid Hybridization—A Practical Approach*, B. D. Hames and S. J. Higgins, Eds., IRL Press, Washington, D.C. Chapter 4, pp. 73-111, 1985). For example, the dot blot method has been developed for multiple analyses of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Baringa, 253 *Science*, pp. 1489, 1991; W. Bains, 10 *Bio/Technology*, pp. 757-758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Baringa, 253 *Science*, pp. 1489, 1991; W. Bains, 10 *Bio/Technology*, pp. 757-758, 1992). SBH makes use of all possible n-nucleotide oligomers (n-mers) to identify n-mers in an unknown DNA sample, which are subsequently aligned by algorithm analysis to produce the DNA sequence (see R. Drmanac and R.

Crkvenjakov, Yugoslav Patent Application #570/87, 1987; R. Drmanac et al., 4 *Genomics*, 114, 1989; Strezoska et al., 88 *Proc. Natl. Acad. Sci.* USA 10089, 1992; and R. Drmanac and R. B. Crkvenjakov, U.S. Patent No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, (United Kingdom Patent Application GB 8810400, 1988; E. M. Southern et al., 13 *Genomics* 1008, 1992), proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency conditions for each oligonucleotide on an array.

Drmanac et al., (260 *Science* 1649-1652, 1993), used the second format to sequence several short (116 bp) DNA sequences. Target DNAs were attached to membrane supports ("dot blot" format). Each filter was sequentially hybridized with 272 labeled 10-mer and 11-mer oligonucleotides. Wide ranges of stringency conditions were used to achieve specific hybridization for each n-mer probe. Washing times varied from 5 minutes to overnight using temperatures from 0° C. to 16° C. Most probes required 3 hours of washing at 16° C. The filters had to be exposed from 2 to 18 hours in order to detect hybridization signals. The overall false positive hybridization rate was 5% in spite of the simple target sequences, the reduced set of oligomer probes, and the use of the most stringent conditions available.

Currently, a variety of methods are available for detection and analysis of the hybridization events. Depending on the reporter group (fluorophore, enzyme, radioisotope, etc.) used to label the DNA probe, detection and analysis are carried out fluorimetrically, calorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. Thus, detection of hybridization events is dependent upon how specific and sensitive hybridization can be made. Concerning genetic analysis, several methods have been developed that have attempted to increase specificity and sensitivity.

One form of genetic analysis is analysis centered on elucidation of single nucleic acid polymorphisms or ("SNPs"). Factors favoring the usage of SNPs are their high abundance in the human genome (especially compared to short tandem repeats, (STRs)), their frequent location within coding or regulatory regions of genes (which can affect protein structure or expression levels), and their stability when passed from one generation to the next (Landegren et al., *Genome Research*, Vol. 8, pp. 769-776, 1998).

A SNP is defined as any position in the genome that exists in two variants and the most common variant occurs less than 99% of the time. In order to use SNPs as widespread genetic markers, it is crucial to be able to genotype them easily, quickly, accurately, and cost-effectively. It is of great interest to type both large sets of SNPs in order to investigate complex disorders where many loci factor into one disease (Risch and Merikangas, *Science*, Vol. 273, pp. 1516-1517, 1996), as well as small subsets of SNPs previously demonstrated to be associated with known afflictions.

Numerous techniques are currently available for typing SNPs (for review, see Landegren et al., *Genome Research*, Vol. 8, pp. 769-776,1998), all of which require target amplification. They include direct sequencing (Carothers et al., *BioTechniques*, Vol. 7, pp. 494-499, 1989), single-strand conformation polymorphism (Orita et al., *Proc. Natl. Acad. Sci.* USA, Vol. 86, pp. 2766-2770, 1989), allele-specific amplification (Newton et al., Nucleic Acids Research, Vol. 17, pp. 2503-2516, 1989), restriction digestion (Day and Humphries, *Analytical Biochemistry*, Vol. 222, pp. 389-395, 1994), and hybridization assays. In their most basic form, hybridization assays function by discriminating short oligonucleotide reporters against matched and mismatched targets. Due to difficulty in determining optimal denaturation conditions, many adaptations to the basic protocol have been developed. These include ligation chain reaction (Wu and Wallace, *Gene*, Vol. 76, pp. 245-254, 1989) and minisequencing (Syvänen et al., *Genomics*, Vol. 8, pp. 684-692, 1990). Other enhancements include the use of the 5'-nuclease activity of Taq DNA polymerase (Holland et al., *Proc. Natl. Acad. Sci.* USA, Vol. 88, pp. 7276-7280, 1991), molecular beacons (Tyagi and Kramer, *Nature Biotechnology*, Vol. 14, pp.303-308, 1996), heat denaturation curves (Howell et al., *Nature Biotechnology*, Vol. 17, pp. 87-88, 1999) and DNA "chips" (Wang et al., *Science*, Vol. 280, pp. 1077-1082, 1998). While each of these assays are functional, they are limited in their practical application in a clinical setting.

An additional phenomenon discovered to be useful in distinguishing SNPs is the nucleic acid interaction energies or base-stacking energies derived from the hybridization of multiple target specific probes to a single target. (see R. Ornstein et al., "An Optimized Potential Function for the Calculation of Nucleic Acid Interaction Energies", in *Biopolymers*, Vol. 17, 2341-2360 (1978); J. Norberg and L. Nilsson, *Biophysical Journal*, Vol. 74, pp. 394-402, (1998); and J. Pieters et al., *Nucleic Acids Research*, Vol. 17, no. 12, pp. 4551-4565 (1989)). This base-stacking phenomenon is used in a unique format in the current invention to provide highly sensitive Tm differentials allowing the direct detection of SNPs in a nucleic acid sample.

Prior to the format of the current invention, other methods have been used to distinguish nucleic acid sequences in related organisms or to sequence DNA. For example, U.S. Pat. No. 5,030,557 by Hogan et al. disclosed that the secondary and tertiary structure of a single stranded target nucleic acid may be affected by binding "helper" oligonucleotides in addition to "probe" oligonucleotides causing a higher Tm to be exhibited between the probe and target nucleic acid. That application however was limited in its approach to using hybridization energies only for altering the secondary and tertiary structure of self-annealing RNA strands which if left unaltered would tend to prevent the probe from hybridizing to the target.

With regard to DNA sequencing, K. Khrapko et al., *Federation of European Biochemical Societies Letters*, Vol. 256, no. 1,2, pp. 118-122 (1989), for example, disclosed that continuous stacking hybridization resulted in duplex stabilization. Additionally, J. Kieleczawa et al., Science, Vol. 258, pp. 1787-1791 (1992), disclosed the use of contiguous strings of hexamers to prime DNA synthesis wherein the contiguous strings appeared to stabilize priming. Likewise, L. Kotler et al., *Proc. Natl. Acad. Sci.* USA, Vol. 90, pp. 4241-4245, (1993) disclosed sequence specificity in the priming of DNA sequencing reactions by use of hexamer and pentamer oligonucleotide modules. Further, S. Parinov et al., *Nucleic Acids Research*, Vol. 24, no. 15, pp. 2998-3004, (1996), disclosed the use of base-stacking oligomers for DNA sequencing in association with passive DNA sequencing microchips. Moreover, G. Yershov et al., *Proc. Natl. Acad. Sci.* USA, Vol. 93, pp. 4913-4918 (1996), disclosed the application of base-stacking energies in SBH on a passive microchip. In Yershov's example, 10-mer DNA probes were anchored to the surface of the microchip and hybridized to target sequences in conjunction with additional short probes, the combination of which appeared to stabilize binding of the probes. In that format, short segments of nucleic acid sequence could be elucidated for DNA sequencing. Yershov further noted that in their system the destabilizing effect of mismatches was increased using shorter probes (e.g., 5-mers). Use of such short probes in DNA sequencing provided the ability to discern the presence of mismatches along the sequence being probed rather than just a single mismatch at one specified location of the probe/target hybridization complex. Use of longer probes (e.g., 8-mer, 10-mer, and 13-mer oligos) were less functional for such purposes.

An additional example of methodologies that have used base-stacking in the analysis of nucleic acids includes U.S. Pat. No. 5,770,365 by Lane et al., wherein is disclosed a method of capturing nucleic acid targets using a unimolecular capture probe having a single stranded loop and a double stranded region which acts in conjunction with a binding target to stabilize duplex formation by stacking energies.

Despite the knowledge of base-stacking phenomenon, applications as described above have not resulted in commercially acceptable methods or protocols for either DNA sequencing or the detection of SNPs for clinical purposes. We provide herein such a commercially useful method for making such distinctions in numerous genetic and medical applications by combining the use of base-stacking principles and electronically addressable microchip formats.

SUMMARY OF THE INVENTION

Methods are provided for the analysis and determination of SNPs in a genetic target. In one embodiment of the invention, SNPs in a target nucleic acid are determined using a single capture site on an electronically addressable microchip (e.g, an APEX type microchip). In this embodiment, both wild type and mutant alleles are distinguished, if present in a sample, at a single capture site by detecting the presence of hybridized allele-specific probes labeled with fluorophores sensitive to excitation at various wave lengths. In another embodiment, base-stacking energies of at least two oligonucleotides are used in conjunction with an APEX type bioelectronic microchip.

The electronically facilitated method using an APEX type microchip offers several advantages over passive-based hybridization assays when base-stacking is employed. First, electronic addressing under low salt conditions in the presence of stabilizer oligomer inhibits rehybridization of amplicon strands in situations where amplification of target nucleic acid is carried out. This obviates the need for asymmetric amplification or other more complex methods of strand separation. Electronically facilitated methods additionally allow multiple different amplicons to be addressed to discrete sites thereby greatly facilitating multiplexing of multiple patients or multiple amplicons on an open microchip.

In one embodiment of our system, the amplicons of the target nucleic acid may be anchored to an electronic microchip capture site (i.e. "amplicon down" format) such that multiple amplicons may be placed at the same capture site. The amplicons may be anchored to the capture site on the microchip by attachment moieties located at the 5' end of the amplicon. Such attachment moieties can be binding agents such a biotin incorporated into one of the amplification primers. The anchored nucleic acids may in turn be probed simultaneously or sequentially.

By way of example, in implementation of the amplicon down format, a target nucleic acid is first amplified, such as by PCR, SDA, NASBA, TMA, rolling circle, T7, T3, or SP6, each of which methods are well understood in the art, using at least one amplification primer oligomer that is labeled with a moiety useful for attaching the amplification product to a substrate surface. In one embodiment, a biotin moiety can be attached at the 5' end of the primer. Following amplification, the labeled amplified dsDNA product may be denatured electronically or thermally and addressed to a specified capture site on the microchip surface, thereby making the amplicon behave as an anchored capture moiety. In a preferred embodiment, the complementary strand to the labeled amplification product (i.e., the non-labeled strand) is kept from reannealing to the labeled product by a "stabilizer" oligomer which is inputted into the process during electronic biasing of the labeled targeted amplicon to the capture site. The use of a "stabilizer" oligomer, as provided for in this invention, is unique in that unlike prior base-stacking inventions, it functionally serves two purposes (i.e., to hinder reannealing of complementary amplicons during electronic addressing of the biotinylated target amplicons, and to provide a base-stacking energy moiety for interaction with the second oligomer. This combined functionality effectively lessens the complexity of SNP determination in a microchip format).

Application of site-specific electronic biasing can allow for directed influencing of the ionic environment at the site of hybridization as well as continuous adjustment of hybridization conditions both during and after hybridization. Such manipulation of electronic environment (specifically the dielectric constant of the solution) can be used to influence directly the base-stacking energies between oligonucleotide probes. Additionally, hybridization is greatly accelerated by the concentration achieved during local electronic addressing. Such a system is also highly flexible in that it allows one to take advantage of both thermal and/or electronic discrimination after hybridization. Moreover, electronic biasing equally facilitates distinguishing hybridization mismatches occurring at the terminal nucleic acid pairs of a hybridized duplex as well as destabilizing mismatches occurring internally (e.g., due to destabilizing caused by misalignment of the base pairs). This ability to detect mismatches allows the current invention to be less restricted in choices for positioning the location of SNP bases on probes although generally, for purposes of this invention, mismatches are desired to occur at the terminal base of a probe. For instance, the SNP relevant base may be incorporated as the terminal base of the reporter probe such that when the stabilizer and reporter probes are annealed to the amplicon, the SNP relevant base will lie adjacent to one of the terminal bases of the stabilizer when both the stabilizer and reporter are annealed adjacently to one another on a target nucleic acid strand.

Sensitivity and robustness may further be enhanced by the additional inclusion of yet another probe (i.e., the "interfering" probe) designed to be complementary to the non-labeled strand of the amplicon. Use of this probe further helps to compete away the undesired non-labeled amplicon strand from reannealing to the labeled strand.

In another format of this system, when the stabilizer probe is anchored (i.e. "capture down" format), the system is also simple and multiple amplicons may be placed at the same capture site. These may then be probed simultaneously or sequentially. Generally, although not exclusively, the stabilizer probe will be anchored to the substrate at its 5' end. Such an arrangement necessarily provides that the SNP base will be complementary to either the 3' base of the stabilizer/capture or the 5' base of the reporter probe. Conversely, if the 3' end of the stabilizer/capture is anchored, then the SNP base will be complementary to either the 5' base of the stabilizer/capture or the 3' base of the reporter probe.

By way of example, in implementation of this capture down format, a target nucleic acid is first amplified, such as by PCR or SDA. The amplified dsDNA product is then denatured and addressed to a specified capture site on the microchip surface that has an anchored stabilizer/capture moiety. In a preferred embodiment, the complementary strand to the desired amplification product strand is kept from reannealing to the desired strand by the stabilizer/capture oligomer that, as described above, serves as a first probe that also participates in base-stacking with a second reporter probe. As in the amplicon down method, the stabilizer/capture oligomer as provided for in this invention is unique in that unlike prior base-stacking inventions, it functionally serves two purposes (i.e., to hinder reannealing of complementary amplicons during electronic addressing of the target amplicons and to provide a base-stacking energy moiety for interaction with reporter oligomer thereby lessening the complexity of SNP determination in a microchip format). As with the target down format, interfering probes may be used. Moreover, multiple amplicons may be probed at any particular capture site.

In yet another format, multiple SNPs in a target sequence may be detected. In this format, either of the above mentioned amplicon down or capture down formats may be employed. In this format, multiple base-stacking may be used to resolve the presence of closely spaced SNPs at a single locus. For example, where two SNPs are closely spaced, at least two short reporter. oligonucleotides may be base-stacked against a longer stabilizer oligonucleotide. Each reporter may be labeled with a different fluorophore specific for the allele that occurs at each site. For instance, if a locus has two SNPs in close proximity to one another, reporter probes incorporating the wild-type and mutant bases of each SNP site, each containing a different fluorophore may be used to determine which allele is present.

In yet another embodiment of the invention, SNPs in a target nucleic acid are determined using combined base-stacking energies derived from both 5' and 3' ends of a single reporter probe. In this embodiment, the target nucleic acid is amplified (such as by PCR and preferably via the strand displacement amplification (SDA) technique) such that two spaced amplicons of the target are generated. The two amplicons (a first and a second amplicon) may be from the same genetic locus wherein the sequences are closely spaced, or may be from divergent or unrelated genetic loci. In either case, both the amplicon down and the capture down formats may be used. In the case where the capture down format is used, the stabilizer/capture is designed as a "bridging" stabilizer/capture probe to capture both amplicons in a spaced apart fashion so that at least one reporter probe, which may or may not contain SNP sequence at one or the other end, can be "nested" between the amplicons. Where the amplicon down format is used, only one of the amplicons is anchored and a "bridging" stabilizer/capture probe having sequence complementary to the anchored amplicon and the non-anchored amplicon is employed to hybridize the amplicons in a spaced apart fashion allowing at least one reporter probe to be nested. Where multiple SNPs are associated at such a loci, more than one SNP containing reporter probe may be nested and take advantage of multiple base-stacking energies.

In the case where the amplicons are from different loci, the amplicons may be brought into close proximity with one another using either an anchored bridging stabilizer/capture probe, or an anchored amplicon and a bridging stabilizer/capture probe as described above. The presence of both amplicon sequences may be detected using a reporter probe designed to nest between the captured amplicons using base-stacking energies to stabilize the reporter hybridization as described above. As with the earlier described formats, the reporter probe may incorporate at either and/or both its 5' and 3' ends SNP or wild-type sequence associated with either or both loci.

In a further embodiment, the SNP containing region may contain multiple SNPs and reporter probes can be designed so that more than one reporter probe is used to nest between the first and second amplicons such that each reporter has at least one nucleic acid base on either its 3' or 5' end corresponding to a SNP. Thus, such a system can benefit from both multiple reporter signals and multiple base-stacking energies from nesting probes that possess either a single base corresponding to either SNP or wild-type at either the 3' or 5' end, or that contain such bases at both 3' and 5' ends, thereby increasing sensitivity.

In another embodiment the stabilizer oligomers are generally 20 to 44-mers and preferably about 30-mers, while the reporter probes are generally 10 to 12-mers and preferably about 11-mers. The lengths of such probes are highly effective in accordance with their use in an electronically addressable microchip format. Reporter probes shorter than 8-mers are generally not functional in the ionic environment of the current system.

In the preferred embodiment of the invention, electronically aided hybridization is utilized in the process. In one aspect, during the hybridization of the nucleic acid target with the stabilizer probe and/or the reporter probe, electronic stringent conditions may be utilized, preferably along with other stringency affecting conditions, to aid in the hybridization. This technique is particularly advantageous to reduce or eliminate slippage hybridization among probes and target, and to promote more effective hybridization. In yet another aspect, electronic stringency conditions may be varied during the hybridization complex stability determination so as to more accurately or quickly determine whether a SNP is present in the target sequence.

Hybridization stability may be influenced by numerous factors, including thermoregulation, chemical regulation, as well as electronic stringency control, either alone or in combination with the other listed factors. Through the use of electronic stringency conditions, in either or both of the target hybridization step or the reporter oligonucleotide stringency step, rapid completion of the process may be achieved. Electronic stringency hybridization of the target is one distinctive aspect of this method since it is amenable with double stranded DNA and results in rapid and precise hybridization of the target to the capture site. This is desirable to achieve properly indexed hybridization of the target DNA to attain the maximum number of molecules at a test site with an accurate hybridization complex. By way of example, with the use of electronic stringency, the initial hybridization step may be completed in ten minutes or less, more preferably five minutes or less, and most preferably two minutes or less. Overall, the analytical process may be completed in less than half an hour.

As to detection of the hybridization complex, it is preferred that the complex is labeled. Typically, in the step of determining hybridization of probe to target, there is a detection of the amount of labeled hybridization complex at the test site or a portion thereof. Any mode or modality of detection consistent with the purpose and functionality of the invention may be utilized, such as optical imaging, electronic imaging, use of charge-coupled devices or other methods of quantification. Labeling may be of the target, capture, or reporter. Various labeling may be by fluorescent labeling, colorimetric labeling or chemiluminescent labeling. In yet another implementation, detection may be via energy transfer between molecules in the hybridization complex. In yet another aspect, the detection may be via fluorescence perturbation analysis. In another aspect the detection may be via conductivity differences between concordant and discordant sites.

In yet another aspect, detection can be carried out using mass spectrometry. In such method, no fluorescent label is necessary. Rather detection is obtained by extremely high levels of mass resolution achieved by direct measurement, for example, by time of flight or by electron spray ionization (ESI). Where mass spectrometry is contemplated, reporter probes having a nucleic acid sequence of 50 bases or less are preferred.

It is yet a further object of this invention to provide methods that may effectively provide for genetic identification.

It is yet a further object of this invention to provide systems and methods for the accurate detection of diseased states, especially clonal tumor disease states, neurological disorders and predisposition to genetic disease.

It is yet a further object of this invention to provide a rapid and effective system and methods for identification, such as in forensics and paternity applications.

Yet a further object of the invention is to identify SNPs in infectious organisms such as those responsible for antibiotic resistance or that can be used for identification of specific organisms.

BRIEF DESCRIPTION OF THE DRAWINGS

FIGS. 4a and 4b represent one embodiment of the method wherein base-stacking energies of multiple reporter probes are utilized. FIG. 4a shows the capture down format while FIG. 4b shows amplicon down format. This multiple base stacking approach is applicable where a target possesses closely spaced SNPs.

DETAILED DESCRIPTION OF THE INVENTION

Figure 1A:
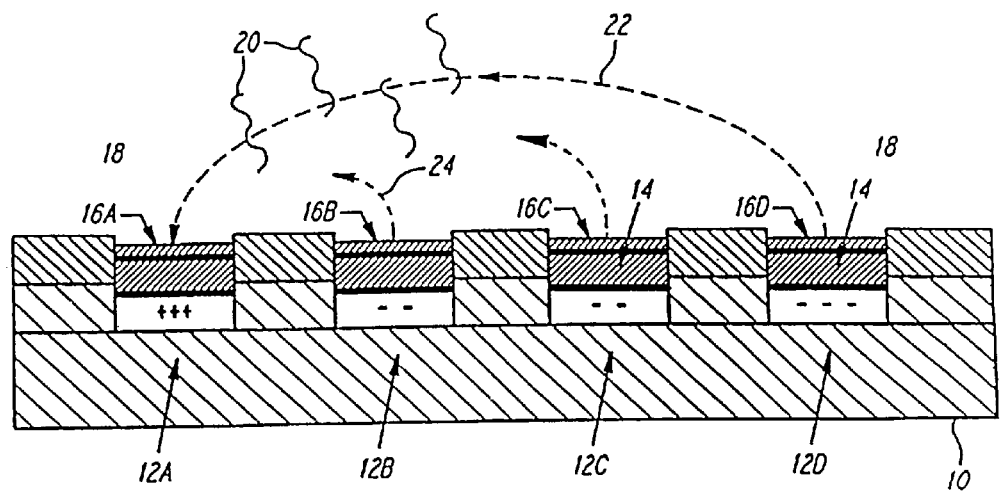
FIG. 1A is a cross sectional view of one embodiment of an active matrix device useful in accordance with the methods of this invention.
Figure 1B:
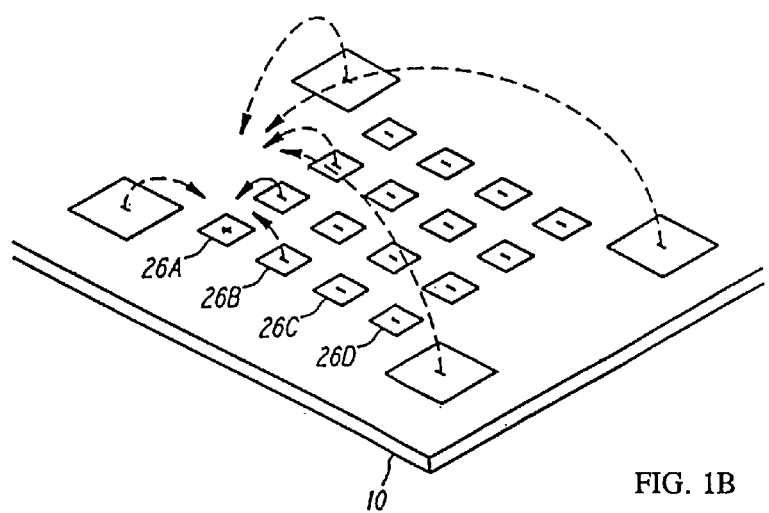
FIG. 1B is a perspective view of an active array device useful with the methods of this invention.

FIGS. 1A and 1B illustrate a simplified version of the active programmable electronic matrix hybridization system for use with this invention. Generally, a substrate 10 supports a matrix or array of electronically addressable microlocations 12. For ease of explanation, the various microlocations in FIG. 1A have been labeled 12A, 12B, 12C and 12D. A permeation layer 14 is disposed above the individual electrodes 12. The permeation layer permits transport of relatively small charged entities through it, but limits the mobility of large charged entities, such as DNA, to keep the large charged entities from easily contacting the electrodes 12 directly during the duration of the test. The permeation layer 14 reduces the electrochemical degradation that would occur to the DNA by direct contact with the electrodes 12, possibility due, in part, to extreme pH resulting from the electrolytic reaction. It further serves to minimize the strong, non-specific adsorption of DNA to electrodes. Attachment regions 16are disposed upon the permeation layer 14 and provide for specific binding sites for target materials. The attachment regions 16 have been labeled 16A, 16B, 16C and 16D to correspond with the identification of the electrodes 12A-D, respectively.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged entity 20 that may be functionalized for specific binding towards the electrode 12. For example, if the electrode 12A were made positive and the electrode 12D negative, electrophoretic lines of force 22 would run between the electrodes 12A and 12D. The lines of electrophoretic force 22 cause transport of charged entities 20 that have a net negative charge toward the positive electrode 12A. Charged materials 20 having a net positive charge move under the electrophoretic force toward the negatively charged electrode 12D. When the net negatively charged entity 20 that has been functionalized for binding contacts the attachment layer 16A as a result of its movement under the electrophoretic force, the functionalized specific binding entity 20 becomes attached to the attachment layer 16A.

Before turning to a detailed discussion of the inventions of this patent, the general matter of terminology will be discussed. The term "single nucleic acid polymorphism" (SNP) as used herein refers to a locus containing simple sequence motif which is a mutation of that locus.

A "hybridization complex", such as in a sandwich assay, typically will include at least two of target nucleic acid, stabilizer probe, and reporter probe.

An "array" as used herein typically refers to multiple test sites, minimally two or more test sites wherein discrimination between wild type and mutant polymorphisms can be carried out for any target sequence at each individual site. The typical number of test sites will be one for each locus to be tested such that heterozygocity or homozygocity for either allele are distinguishable at each site. The number of loci required for any particular test will vary depending on the application, with generally one for genetic disease analysis, one to five for tumor detection, and six, eight, nine, thirteen or more for paternity testing and forensics. The physical positioning of the test sites relative to one another may be in any convenient configuration, such as linear or in an arrangement of rows and columns.

In one mode, the hybridization complex is labeled and the step of determining amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the detection, either labeled or unlabeled, is quantified, which may include statistical analysis. The labeled portion of the complex may be the target, the stabilizer, the reporter or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Labeling may further be accomplished by colormetric labeling, bioluminescent labeling and/or chemiluminescent labeling. Labeling further may include energy transfer between molecules in the hybridization complex by perturbation analysis, quenching, electron transport between donor and acceptor molecules, the latter of which may be facilitated by double stranded match hybridization complexes (See, e.g., Tom Meade and Faiz Kayyem, Electron Transfer Through DNA:Site-Specific Modification of Duplex DNA with Ruthenium Donors and Acceptors, Angew. Chem. Int. Ed., England, Vol. 34, #3, pp. 352-354, 1995). Optionally, if the hybridization complex is unlabeled, detection may be accomplished by measurement of conductance differential between double stranded and non-double stranded DNA. Further, direct detection may be achieved by porous silicon-based optical interferometry or by mass spectrometry.

The label may be amplified, and may include for example branched or dendritic DNA. If the target DNA is purified, it may be unamplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

The target DNA may be from a source of tissue including but not limited to hair, blood, skin, sputum, fecal matter, semen, epithelial cells, endothelial cells, lymphocytes, red blood cells, crime scene evidence. The source of target DNA may also include normal tissue, diseased tissue, tumor tissue, plant material, animal material, mammals, humans, birds, fish, microbial material, xenobiotic material, viral material, bacterial material, and protozoan material. Further, the source of the target material may include RNA. Further yet, the source of the target material may include mitochondrial DNA.

Base-stacking is dependent on the interactions of the ring structure of one base with the base ring of its nearest neighbor. The strength of this interaction depends on the type of rings involved, as determined empirically. While the applicants do not wish to be bound by any theory, among the possible theoretical explanations for this phenomenon are the number of electrons available between the two bases that participate in Pi bond interactions and the efficiency of different base combinations that exclude water from the interior of the helix, thereby increasing entropy. Although the above models are consistent with current data, the possible mechanisms of stacking interactions are not limited to these concepts.

It has also been observed that modification of bases involved in base-stacking interactions can strengthen Pi bonding, or stacking, between them. As one might predict from the models described above, these modifications provide more electrons for use in Pi bonding and/or an increase to the surface area of the rings, thereby increasing the area of hydrophobicity between the stacked bases. The current system can be modulated in a manner predicted by base-stacking theory and be used to predict additional changes for altering Pi electron behavior thereby underscoring that the mechanism of the invention may be dependent on the nature of Pi bonding between juxtaposed bases.

In addition to taking advantage of the naturally selected base-stacking interactions, it may be predicted that base modifications that increase the number of electrons in the ring or enlarge the hybdrophobic area would also increase discrimination of match from mismatch hybrids. Taking such information into account we have developed a novel SNP scoring method. It utilizes a combination of electronic-mediated nucleic acid transportation of an amplified target, passive heat denaturation of short fluorescent oligo reporters, and base-stacking energies. Sosnowski et al., *Proc. Natl. Acad. Sci.* USA, Vol. 94, pp. 1119-1123, (1997) have previously shown that charged DNA molecules can be transported, concentrated, and hybridized on a microchip by use of a controlled electric field. By taking advantage of an active microchip and base-stacking energies, we are able to efficiently target and analyze numerous SNPs with a high level of discrimination.

To demonstrate the efficacy of this new technique, we developed two model systems. The first is based on Hereditary Hemochromatosis, an autosomal recessive disorder that may lead to cirrhosis of the liver, diabetes, hypermelanotic pigmentation of the skin, and heart failure. The disease is linked to a G to A nucleotide transition at position 8445 in the HLA-H gene (Feder et al., *J. Biol. Chem.*, Vol. 272, pp. 14025-14028, 1997). This locus was subsequently renamed HFE. The second assay centers on the Factor V gene. A mutation at position 1,691 (G to A substitution) leads to an increased risk of venous thrombosis (Bertina et al., *Nature*, Vol. 369, pp. 64-67, 1994). A SNP scoring methodology that offers both high throughput and cost effectiveness should allow implementation of routine tests for detecting individuals at risk for these, as well as other diseases that correlate to known SNPs, before disease onset. The utility of SNPs as genetic markers is therefore dependent, at least in part, upon the ability to provide accurate scoring of SNPs quickly. We have developed a novel scoring methodology, which fits these criteria.

Using an active microarray, we are able to miniaturize and accelerate the process of DNA transportation and hybridization. Moreover, the instrument in which the experiments are carried out is automated, which further streamlines this SNP scoring process. Further, this new methodology offers significant advancement in the fidelity of SNP scoring. We have accurately called every unknown sample tested, be it Hemochromatosis or Factor V. We have also successfully analyzed the Factor V SNP from each strand (FIG. 8 and FIG. 12), demonstrating the flexibility of the dual fluorescent base-stacking assay. It allows us to probe either strand, providing the opportunity to generate the most favorable (i.e., most energetic) stacking configuration. This ensures optimal discrimination.

A frequent problem in analyzing SNPs via conventional hybridization assays is the inability to call heterozygotes with 100% accuracy. Missing one of the two alleles can be as serious as a complete miscall. This problem usually arises when one of the allele-specific reporters (wild-type or mutant) is slightly more thermodynamically stable, often leading to ambiguous results.

Figure 11:
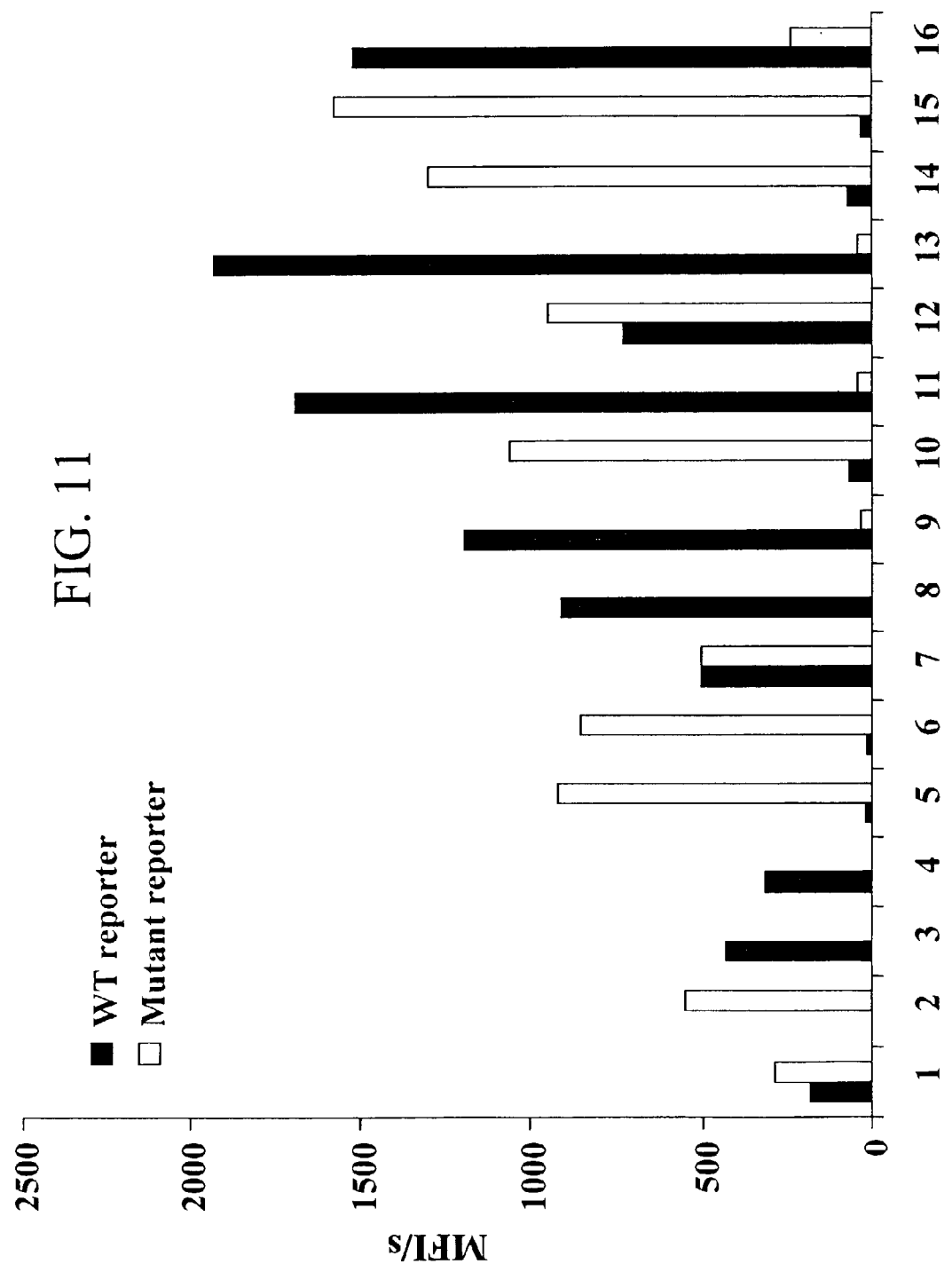
FIG. 11 is a chart illustrating that the allele content of unknown Hemochromatosis samples is readily determinable. Sixteen amplified, unknown Hemochromatosis samples were tested using 1 µM Hemochromatosis stabilizer oligo (Seq. Id. No. 8). The samples and stabilizer were electronically targeted to individual capture sites on a 25-site microarray. Biasing was carried out for 4 minutes using an alternating current of 700 nAmps/site at 38 msec '+' and 10 msec '−'. Following passive reporting of the two allele-specific reporters (i.e., wild-type Seq. Id. No. 11 or mutant Seq. Id. No. 12), thermal discrimination was achieved at 29° C. The histogram represents the mean fluorescent intensities minus background (signal intensity from a mock targeted site). Results show that samples 1, 7, and 12 are heterozygous, samples 3, 4, 8, 9, 11, 13, and 16 are homozygous for wild type, and samples 2, 5, 6, 10, 14, and 15 are homozygous for mutant.

By differentiating reporters based on both base-stacking energies and number of hydrogen bonds, we have been able to essentially normalize and enhance the stability of the correct reporters, thereby allowing easy discrimination between homozygotes and heterozygotes. On average, an amplified homozygote sample, such as for Hemochromatosis and Factor V, yields discrimination values greater than 15-fold between match and mismatch. In the 46 samples analyzed, the poorest discrimination for a homozygote was ~6.3-fold. On the other hand, heterozygotes yielded ratios of approximately 1:1, and never more than 2:1. Since the discrimination values are so disparate between homozygotes and heterozygotes, it allows us to call homozygotes even if the amplification is biased towards one strand (see FIG. 11).

We initially chose Hemochromatosis and Factor V to be analyzed as each SNP has been linked to a specific and important disease (Feder et al., 1996 Supra; Bertina et al., 1994 Supra). Moreover, both conditions are relatively prevalent in society. A recent AACC bulletin report suggests that Hemochromatosis may be more prevalent than previously believed (American Association for Clinical Chemistry, Inc., *Clinical Laboratory News*, Vol. 25, number 2, pp. 16, February 1999). The use therefore of a methodology for early genetic testing of people at risk for these two afflictions should become an important tool in determining people that are heterozygous or homozygous for the mutant allele. This will allow early treatment, thereby improving quality of life.

We have demonstrated that SNP discrimination by the dual fluorescent base-stacking format works for two different genes. Moreover, we have determined that the method should function in a universal approach in that every possible mismatch for a reporter probe and target with respect to a stabilizer probe is distinguishable. (see Table 2). As shown each combination has strong discrimination values except for one combination. The one example showing a weak discrimination value (2.97) is of little consequence because the opposite strand combination can be substituted in an actual test case.

Figure 2:
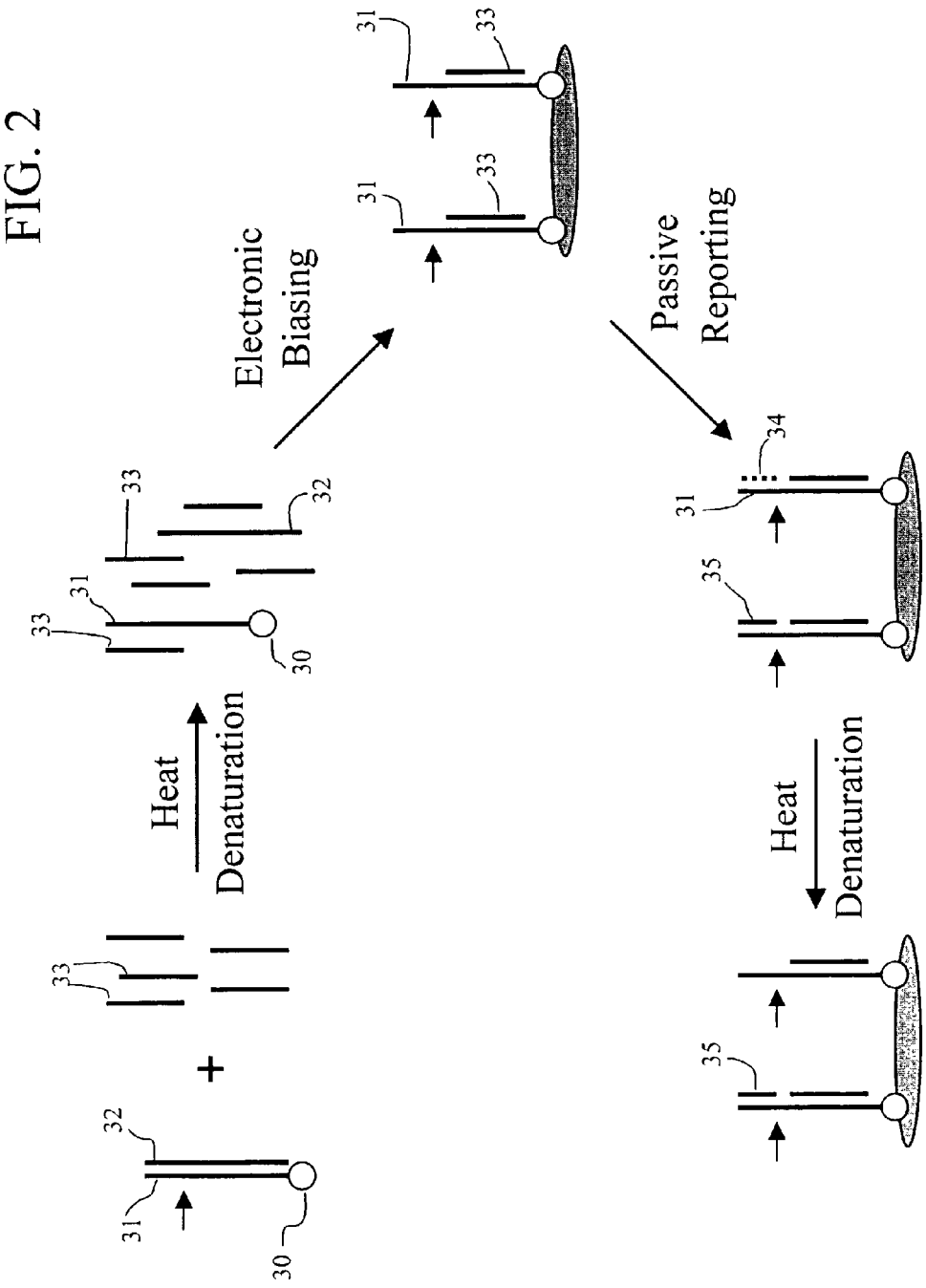
FIG. 2 is a schematic representation of one embodiment of the method of electronic SNP scoring by a dual fluorescent base-stacking format wherein the target amplicon population comprises wild-type and/or mutant alleles. In this format, one of the target strands is anchored to the capture site ("amplicon down" format). As shown, wild type and mutant alleles may be probed at a single capture site. Where the target includes both alleles, (i.e., heterozygote) reporter probes corresponding to each allele will be detected. Where only one allele is present, (i.e., homozygote) only one reporter probe will be detected. The figure represents detection of a homozygote population.

As a general description, this invention is best described in conjunction with FIG. 2. Initially, the sample containing a nucleic acid population representing one of or both wild type and mutant alleles is amplified with two primers, one being biotinylated (i.e., amplicon down format). Following the removal of salt, the amplification product 31, with its biotinylated moiety, and the complementary strand 32 are diluted 1:2 in a final concentration of 50 mM histidine. This solution also contains 1 µM of stabilizer oligomer 33. The stabilizer oligomer 33 is generally a 30-mer that is 100% complementary to both wild type and mutant alleles. This stabilizer directly abuts the polymorphism site on the target amplicon such that when a perfectly matched mutant reporter 34 or wild-type 35 is added to the system, base-stacking will be present.

Following introduction of the stabilizer, the reaction solution is heated to 95° C. for 5 minutes to allow the amplicon to denature. This sample, after cooling, is then electronically biased to the capture site of choice on an APEX type microchip. After biasing, the biotinylated amplicon strand 31 is attached to the microchip capture site via the biotin/streptavidin interaction with the permeation layer of the microchip. The 30-mer stabilizer oligomer 33 is hybridized to the amplicon strand 31 through hydrogen bonds.

The 30-mer stabilizer 33 effectively blocks the binding of the fully complementary nonbiotinylated amplicon strand 32 due the relative higher concentration of the stabilizer 33 (The stabilizer is at 1 µM concentration whereas the amplicon is generally between 500 pM and 5 nM).

Once the different amplicons (such as in a multiplex assay) have been electronically biased to their respective capture sites, reporting (using oligomers that are generally the probes that are labeled) is carried out. 1 uM of both wild type 35 and mutant 34 reporters (each identical with respect to 9 to 11 bases of the wild type with the terminal base, either 3' or 5', (or both), corresponding to either the mutant or the wild-type base) in 50 mM NaPO4/500 mM NaCl (high salt buffer) is allowed to incubate on the microchip for 3-5 minutes. Following incubation of the reporter probes 34 and 35, discrimination is achieved by heating the microchip about 4° C. below melting temperature of the perfectly matched reporter/amplicon in 50 mM NaPO4 (low salt buffer). Imaging is then performed using two different lasers, one corresponding to the fluorophore on the wild-type reporter and one to the fluorophore on the mutant reporter. From these signal intensities, backgrounds are subtracted and specific activities are taken into account. A ratio of wild type to mutant signal is achieved from which the allelic composition of the amplicon products are determined.

EXAMPLE I a. Assay for the Discrimination of Single-Nucleotide Polymorphisms.

SNP scoring on an active matrix chip was accomplished as exemplified by the methodology illustrated in FIG. 2. The target was amplified with one biotinylated primer. A high concentration of 30-mer stabilizer oligo was added to the denatured amplicon and the mixture was electronically addressed to capture sites of interest on the array. Because DNA could be rapidly concentrated and hybridized, this process took place in a period as short as two minutes. The stabilizer oligomer was complementary to the biotinylated amplicon strand (the strand being probed). First, the stabilizer prevented the rehybridization of the complementary target amplicon strand thereby allowing the two allele-specific fluorescently-labeled reporter oligos access to the biotinylated strand. Second, along with the reporter oligos, it conferred base-stacking energy.

The stabilizer oligo was designed such that its 5'-terminus abutted the polymorphism of interest. The reporter oligos, one perfectly complementary to the wild type allele and one to the mutant allele, were designed such that their 3'-termini encompassed the polymorphism. When the stabilizer and reporter oligomers perfectly matched the target in an adjacently hybridized format, strong base-stacking energy phenomena were realized. In this system the reporters were 11 bp in length which provided excellent base-stacking differential signal between perfect matches and SNP mismatches, notwithstanding the results disclosed by prior researchers as mentioned above. Essentially, the mismatched reporter has one less nucleotide hydrogen bonded to its complement than the matched reporter. Upon stringent discrimination conditions, the perfectly matched reporter remains bound to its complement while the mismatched reporter readily dissociates.

In situations where the area of the target amplicon to be probed is closer to the 5' end of the amplicon, the stabilizer can be designed to anneal to the amplicon at a position nearer the 3' end of the amplicon thereby necessitating that the 3'-terminus of the stabilizer abut the polymorphism and the 5'-terminus of the reporter encompass the polymorphism.

b. The Stabilizer Oligo Enhances SNP Discrimination by Imparting Base-Stacking Energy.

To investigate the importance of employing stabilizer oligomers in this SNP scoring methodology, five unknown Factor V samples were analyzed in the presence or absence of the stabilizer probe. After electronically addressing the denatured target nucleic acid, the microchip was washed with 0.5×SSC, pH 12 to remove any rehybridized complementary strands. Stabilizer oligo was then electronically biased to capture sites for different time intervals to titrate their levels.

Figure 8:
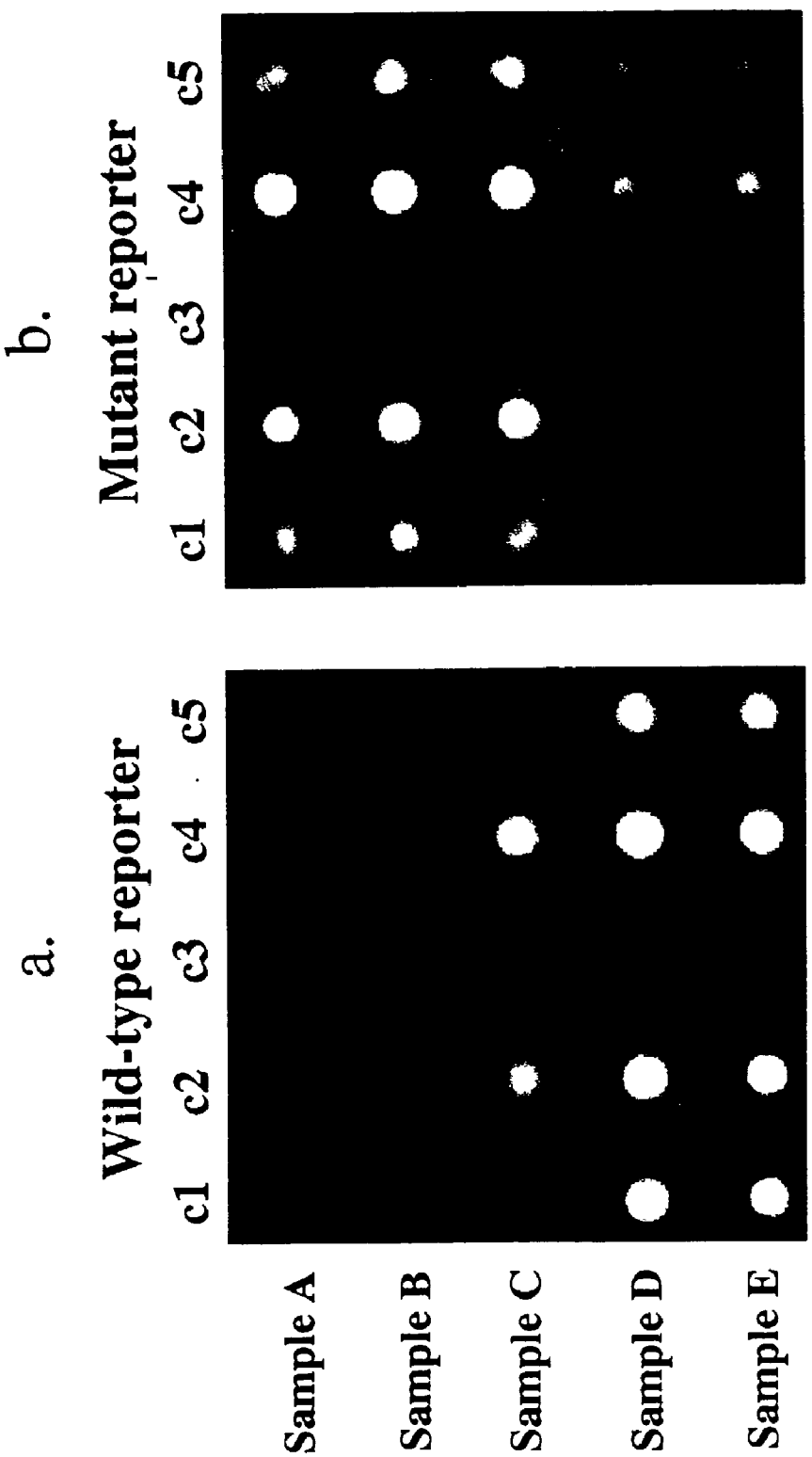
FIGS. 8a and 8b are photographs showing hybridization results on the same microchip capture sites using reporter probes corresponding to wild type, and mutant alleles labeled with fluorophores sensitive to two different wavelengths. Results show that homozygous mutant, homozygous wild type, and heterozygosity is clearly detectable. Specifically, the importance of stabilizer oligomer for scoring Factor V SNPs is represented. Five unknown Factor V samples (labeled A through E) were amplified using primers Seq. Id. No. 1 (Biotin-TGTTATCACACTGGTGCTAA) and Seq. Id. No. 2 (ACTACAGTGACGTGGACATC). The amplification product was then electronically targeted to 4 capture sites (columns 1,2, 4, and 5) using a direct current of 400 nAmps/site for 2 minutes. Column 3 was mock targeted and served as background control. The array was then treated with 0.5× SSC, pH 12 for 5 minutes to denature any rehybridized amplified products. Next, 125 nM Factor V stabilizer oligo, Seq. Id. No. 3 (TAATCTGTAAGAGCAGATCCCTGGACAGGC), was electronically biased using direct current of 400 nAps/site to all capture sites in column 1 for 15 seconds, column 2 for 30 seconds, and column 4 for 60 seconds. Column 5 was biased for 60 seconds with buffer only. Final discrimination of the allele-specific reporters at each capture site was achieved at 32° C. in our low salt buffer. The reporter oligomers were a CR6G labeled wild type reporter, Seq. Id. No. 4 (GAGGAATACAG-CR6G), and a Far-Red labeled mutant reporter, Seq. Id. No. 5 (AAGGAATACAG-Far-Red). Results indicate that Samples A and B are homozygous for mutant, Sample C is heterozygous for mutant and wild type, and Samples D and E are homozygous for wild type.

The wild type and mutant reporters, coupled to different fluorophores, were then passively hybridized to the target:stabilizer complex. This was followed by stringent discrimination achieved by increasing the temperature of a low salt wash buffer. Fluorescent signals were then measured at the two appropriate wavelengths to detect the wild type and mutant reporters. The results of this experiment are shown in FIG. 8. Discrimination values are given in Table 1.

TABLE 1

Role of stabilizer oligo on SNP discrimination.

| Sample | no stabilizer | 15" stabilizer | 30" stabilizer | 60" stabilizer |
|---|---|---|---|---|
| A | 1:>100 | 1:>100 | 1:>100 | 1:>100 |
| B | 1:>100 | 1:>100 | 1:>100 | 1:47.7 |
| C | 1:3.31 | 1:1.55 | 1:1.44 | 1:1.53 |
| D | 3.51:1 | 10.1:1 | 16.2:1 | 13.9:1 |
| E | 3.73:1 | 8.63:1 | 10.7:1 | 12.9:1 |

(All discrimination values are reported as wild type signal intensity to mutant signal intensity.)

The significance of the stabilizer oligo can most clearly be shown for Sample C, a Factor V heterozygote. Column 5, which received no stabilizer, shows a clear mutant signal but essentially no wild type signal. Discrimination values were roughly 3.3:1 mutant to wild type. When compared with wild type samples (D and E), the discrimination value in the absence of stabilizer was almost identical, 3.5:1 and 3.7:1 wild type to mutant, respectively, making it essentially impossible to differentiate a Factor V heterozygote from wild type. In contrast, Sample C complexed with the most stabilizer oligo (column 4), was a clear heterozygote (1:1.5 mutant to wild type), while samples D and E were clear wild types (13.9:1 and 12.9:1, respectively).

These results demonstrate that base-stacking energies supplied by the abutment of the stabilizer and reporter can be used to enhance discrimination of reporter oligos that are either perfectly matched or mismatched by as little as one base pair. Moreover, the results indicate that mismatches involving more than one base pair (i.e., one at either end of the reporter) would equally be distinguishable.

The increased stabilization for perfectly matched complexes can also be demonstrated in the augmented signal intensities of samples that received more stabilizer oligo (compare Factor V mutant samples A and B, column 1 (least stabilizer) and column 4 (most stabilizer) FIG. 8). The discrimination values (Table 1) in the presence of stabilizer are excellent. The allelic makeup of all five unknown Factor V samples are unambiguous with A and B being homozygous mutant, C being a heterozygote, and D and E being homozygous wild type. All results were independently confirmed by allele-specific amplification.

Figure 9:
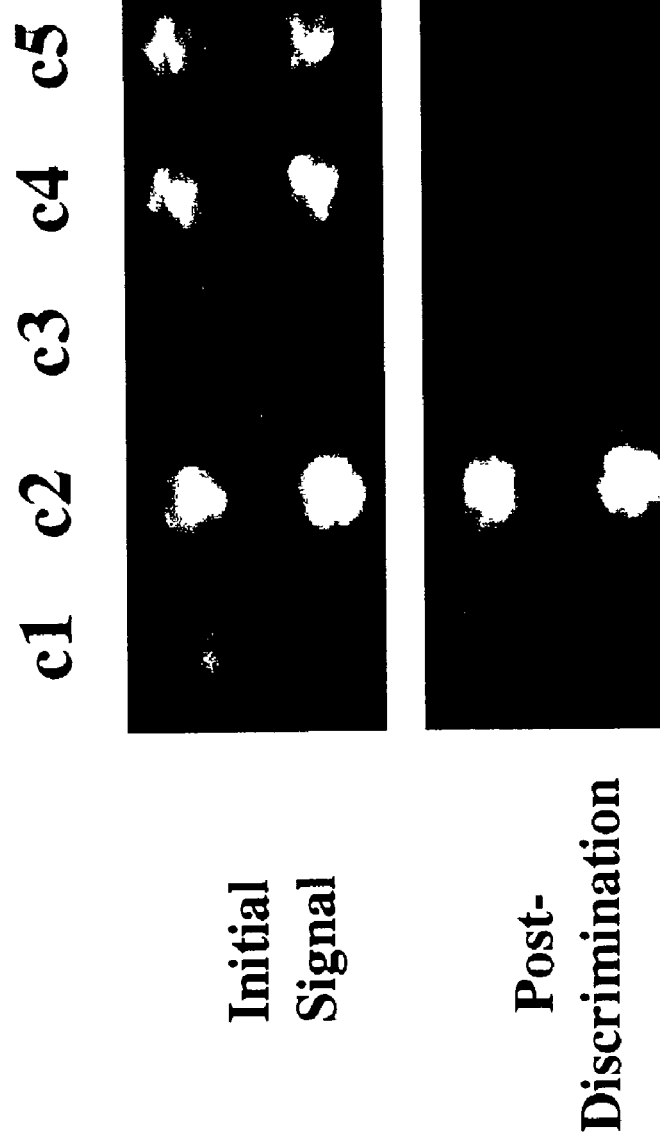
FIG. 9 is a photograph showing that base-stacking energy stabilizes oligo reporters. Wild type Hemochromatosis sample was amplified using Seq. Id. No. 6 (Biotin-TGAAG-GATAAGCAGCCAAT) and Seq. Id. No. 7 (CTCCTCT-CAACCCCCAATA). The amplified sample was then mixed with either (i), no stabilizer oligo (column 1); (ii), 1 µM of the standard Hemochromatosis stabilizer oligomer in which case the stabilizer hybridizes adjacent to the reporter probe (column 2), Seq. Id. No. 8 (GGCTGATCCAGGCCTGGGT-GCTCCACCTGG); (iii), a stabilizer oligomer that hybridizes to target with a one base gap between the stabilizer and reporter probe (column 4), Seq. Id. No. 9 (GGGCTGATC-CAGGCCTGGGTGCTCCACCTG); or (iv), a stabilizer oligomer Seq. Id. No. 10 (CACAATGAGGGGCTGATCCAG-GCCTGGGTG) resulting in a 10 bp gap between itself and the reporter (column 5). The resulting samples were biased simultaneously to two capture sites for a total of 4 minutes using a biased alternating current protocol wherein 700 nAmps/site at 38 msec '+' and 10 msec '−' was used. Column 3 was mock targeted and served as a background control. After passive reporting with wild type reporter oligomer, Seq. Id. No. 11 (CACGTATATCT-CR6G), thermal discrimination of the reporter probe was attained at 32° C. in our low salt buffer. The images represent the wild type reporter only, both before (initial signal) and after thermal denaturation (post-discrimination). Only in the situation where the stabilizer and reporter probes were adjacent was the hybridization stabilized. The same result is obtainable using mutant (data not shown).

To unequivocally illustrate that base-stacking energies are conferring the enhanced discrimination values, stabilizer oligomers to Hemochromatosis were designed such that a 1 bp or a 10 bp gap would exist between the stabilizer and reporter. These stabilizers were compared with the standard Hemochromatosis stabilizer that directly abuts the reporter. In this experiment, the stabilizer oligomers and sample, specifically a Hemochromatosis wild type, were concomitantly biased to duplicate capture sites. The results are shown in FIG. 9. In the case of no stabilizer (column 1), the initial wild type reporter signal is substantially reduced. The columns which received the standard stabilizer (column 2), the stabilizer leading to a 1 bp gap (column 4), and the stabilizer leading to a 10 bp gap (column 5), all had comparable initial signals. However, upon thermal discrimination, only the wild type reporter on the capture sites biased with the standard stabilizer remained, demonstrating that base-stacking energies were stabilizing the shorter reporter.

c. A Stabilizer Oligo Prevents Rehybridization of the Complementary Nucleic Acid Strand.

A difficulty in directing one strand of an amplification product following denaturation to a specific capture site of interest is that under most conditions the complementary strand will anneal back to its cognate partner. In an attempt to circumvent this problem, a high concentration of stabilizer oligomer was included with the amplification product during electronic addressing.

Figure 10:
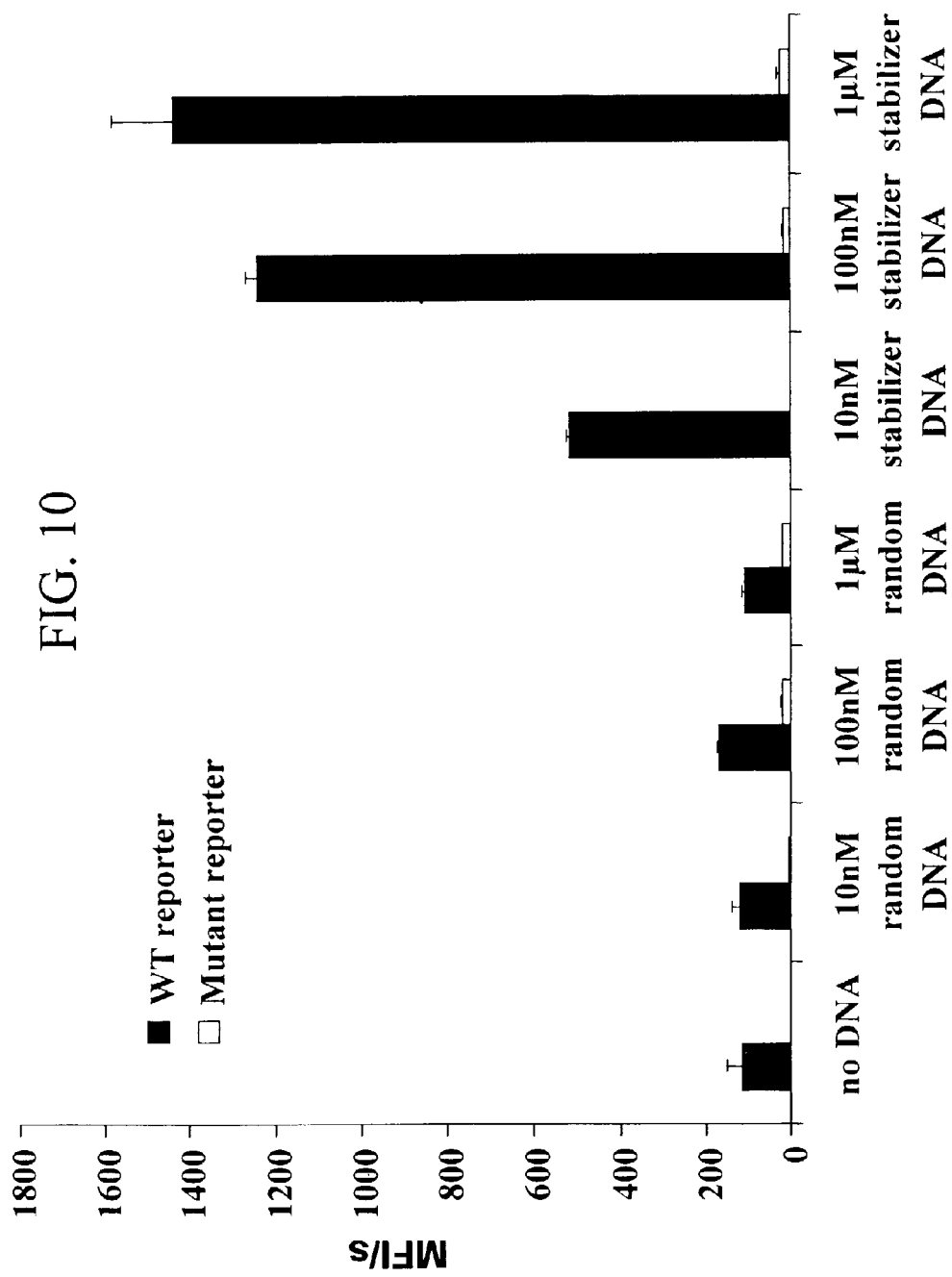
FIG. 10 shows the impact of stabilizer oligo on signal intensity. An amplified wild type Hemochromatosis sample was mixed with either the standard 30-mer stabilizer oligo (Seq. Id. No. 8), non-complementary random DNA (six different 20-mer to 24-mer oligos), or no DNA (water) at three concentrations (10 nM, 100 nM, and 1 µM). Each combination was biased to duplicate capture sites for 4 minutes using a biased alternating current protocol 800 nAmps/site at 38 msec '+' and 10 msec '−'. Capture sites that received either no DNA or random DNA were subsequently biased for 1 minute with 125 nM stabilizer oligo, while capture sites that already received stabilizer were biased for 1 minute with buffer only. Biasing conditions were direct current at 400 nAmps/site. The histogram represents the signal intensities of both the wild type (Seq. Id. No. 11) and mutant (Seq. Id. No. 12, TACGTATATCT-Far Red) reporters post-discrimination, achieved at 28° C. Background from capture sites addressed with no DNA was subtracted.

Various concentrations of Hemochromatosis stabilizer oligomer were combined with a wild type Hemochromatosis amplification product sample. These samples were compared to the identical wild type Hemochromatosis sample containing either no stabilizer oligomer or non-complementary nucleic acid. After initial biasing, the capture sites addressed without stabilizer were then re-addressed with a saturating level of stabilizer oligo. Capture sites initially targeted with amplicons plus stabilizer, were electronically addressed with buffer solution only. Reporter hybridization was carried out, followed by stringent washing. The final results are shown in FIG. 10.

In each case, high levels of discrimination were achieved. All permutations had a wild type to mutation ratio of greater than five-fold. However, signal on capture sites where stabilizer was simultaneously applied with amplification product, was significantly more robust. This suggests that the stabilizer bound to the biotinylated amplicon strand, and prevented the opposite amplified strand from rehybridizing. This result is somewhat surprising, since the amplification product hybrid (a 229-mer) would be expected to be much more stable than the stabilizer hybrid (a 30-mer). At equimolar ratios (approximately 1 nM), hybridization by the complementary amplicon strand would dislodge the bound stabilizer and block the reporter oligo from binding to the biotinylated strand. However, at higher molar ratios and the electronic conditions used in this assay, the stabilizer competes-out one strand of the amplicons. This result is also confirmed by the data in FIG. 9. Prediscrimination signals (initial) were substantially higher in the presence of a complementary stabilizer oligo, even one resulting in a gap between the stabilizer and reporter (compare columns 2, 4 and 5 to column 1).

d. Analysis of Unknown Hemochromatosis Samples.

Use of SNPs as genetic markers requires that their presence in a sample be accurately and quickly determined via a high throughput system. By taking advantage of an electric field to rapidly concentrate and hybridize nucleic acid, we are able to achieve discrimination results very efficiently. The accuracy of this SNP scoring method is demonstrated in the following experiment.

Sixteen unknown Hemochromatosis samples were amplified. Along with stabilizer oligo, each were electronically targeted to one capture site of a 25 site array. After allowing both wild type and mutant Hemochromatosis reporter oligos to passively hybridize to the amplified sample:stabilizer complex, stringent washing conditions were applied. The results, depicted in histogram form, are displayed in FIG. 11.

Assuming that a heterozygote should be roughly 1:1 wild type to mutant signal, it is clear that three of the unknown samples, 1, 7, and 12, were heterozygotes. Our criteria for calling a homozygote is that it should have at least five-fold more signal remaining from the perfectly matched reporter than the mismatched reporter. Following this criteria, it is easy to call samples 3, 4, 8, 9, 11, 13, and 16 as Hemochromatosis wild types and samples 2, 5, 6, 10, 14, and 15 as Hemochromatosis mutants. In fact, only sample 16 (~6.3-fold) had a discrimination value of less than 15-fold. All results were independently confirmed by restriction analysis followed by gel electrophoresis. By discriminating SNPs using base-stacking energies, we have been able to correctly call 37/37 Hemochromatosis samples and 9/9 Factor V unknowns.

e. Analysis of Hemochromatosis and Factor V Samples on a Single Capture Site.

In another embodiment of the invention, throughput is increased for multiplex analysis of target sequences by electronically targeting more than one amplicon product to a single capture site. This both enhances the speed of the assay and increases the information yield of the microarray.

Figure 12:
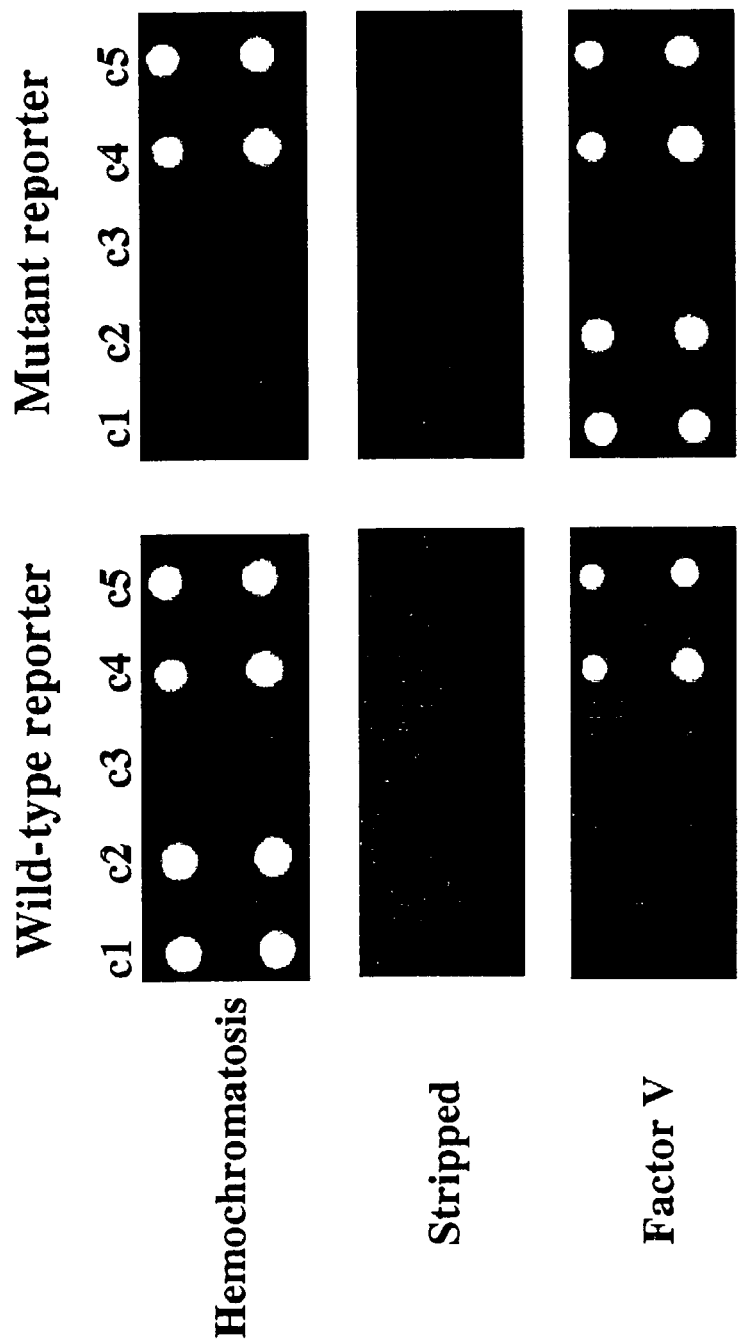
FIG. 12 is a photograph showing multiplex analysis of Hemochromatosis and Factor V. In this figure, the results for Factor V were derived from use of the opposite strand to the results shown in FIG. 8. Two known Hemochromatosis and Factor V samples were each amplified individually. In this case, Factor V samples were amplified using primers Seq. Id. No. 13 (Biotin-ACTACAGTGACGTGGACATC) and Seq. Id. No. 14 (TGTTATCACACTGGTGCTAA). The amplification products were then combined together along with 1 µM of each of their 30-mer stabilizer oligos (i.e., Seq. Id. No. 8 and Seq. Id. No. 15 (TTACTTCAAGGACAAAATACCTG-TATTCCT)). Each mixture was electronically biased in quadruplicate for 4 minutes using a biased alternative current of 700 nAmps/site at 38 msec '+' and 10 msec '−'. The capture site in column 1 and 2 received a Hemochromatosis wild type and Factor V mutant, while the sites in column 4 and 5 were targeted with both Hemochromatosis and Factor V Heterozygotes. Column 3 was the background control. Reporting was done sequentially, first with the allele-specific Hemochromatosis reporters (Seq. Id. Nos. 11 and 12) and then the allele-specific Factor V reporters (Seq. Id. Nos. 16 (CGCCTGTC-CAG-CR6G) and 17 (TGCCTGTCCAG-Far Red). Before Factor V reporters were passively hybridized, all remaining Hemochromatosis reporters were stripped from the microarray. In this experiment, heat discrimination in the low salt buffer was achieved at 28° C. for Hemochromatosis and 43° C. for Factor V. Stripping was carried out at 55° C. in our low salt buffer. The images represent the fluorescent signals from both the wild type and mutant reporters, all after thermal denaturation.

After amplification, we mixed together known Hemochromatosis and Factor V samples and their respective stabilizer oligos. Two such combinations were tested in quadruplicate. One contained a Hemochromatosis wild type and a Factor V mutant (FIG. 12, columns 1 and 2). The other contained Hemochromatosis and Factor V heterozygotes (FIG. 12, columns 4 and 5). Reporting and stringent washing was carried out first with Hemochromatosis reporters, followed by repeating the process with Factor V reporters. In each case, the results were as expected and easy to score. Since both set of reporters contained the same fluorophores, success of this multiplexing required complete removal of all bound Hemochromatosis reporters prior to the addition of the Factor V reporters. Note the complete lack of signal on the array after stripping, which was achieved by elevating the temperature in a low salt buffer.

The reason thermal discrimination was achieved at a much higher temperature for Factor V than previously shown (43° C. FIG. 12 vs. 32° C. in FIG. 8) is that the opposite strand was being interrogated. In this case, the Factor V reporters were significantly more GC rich, and thus, more thermally stable. By analyzing two PCR amplicons on a single capture site, we effectively double our throughput per unit time and per chip.

f. Universality of the Base-Stacked SNP Scoring Method.

We have successfully demonstrated that a SNP scoring method which takes advantage of electronic biasing and a reporter that is stabilized by base-stacking energies is indeed feasible. Besides the examples shown for Hemochromatosis and Factor V, we demonstrate that this assay can be applied universally to discriminate any SNP. Specifically, we designed a set of oligos around the Hemochromatosis polymorphism such that every possible base-stacking combination could be analyzed. The results from these experiments are compiled in Table 2.

TABLE 2

Universality of SNP discrimination by base stacking energies.

| Stabilizer[b] | Reporter[a] | | | | | | | |
|---|---|---|---|---|---|---|---|---|
| | A | | C | | G | | T | |
| A | A[c] | >100[d] | A | 29.5 | A | >100 | C | 8.38 |
| A | C | >100 | C | >100 | G | 43.8 | G | 7.98 |
| A | G | 21.6 | T | >100 | T | >100 | T | 9.52 |
| C | A | 51.6 | A | 40.3 | A | 89.9 | C | 8.85 |
| C | C | 50.1 | C | 64.3 | G | >100 | G | 15.5 |
| C | G | >100 | T | 34.6 | T | 86.8 | T | 37.0 |
| G | A | >100 | A | 36.9 | A | 68.8 | C | 35.1 |
| G | C | >100 | C | >100 | G | 26.2 | G | 24.8 |
| G | G | 11.7 | T | 92.3 | T | 51.0 | T | 11.0 |
| T | A | 10.1 | A | 22.0 | A | 37.9 | C | 15.6 |
| T | C | 56.9 | C | >100 | G | 34.4 | G | 13.7 |
| T | G | 2.79 | T | 51.9 | T | 28.5 | T | 6.46 |

[a]Reporter nucleotide represents the 5'-terminus of the reporter oligo.
[b]Stabilizer nucleotide represents the 3'-terminus of the stabilizer oligo.
[c]Nucleotide represents mismatched nucleotide on target sequence. For example, if the reporter is an A, then the match on the target nucleic acid is a T, and the mismatches are A, C, and G.
[d]Values are fold discrimination between the matched target nucleic acid and designated mismatch.

In all cases but one, the discrimination between match and mismatch was greater than five-fold, and in most cases it was greater than 20-fold. This demonstrates that it is easy to differentiate homozygote wild type from homozygote mutant from heterozygote for any possible SNP, regardless of the polymorphism.

The one instance where this assay yielded poor discrimination (only 2.8-fold) was to be expected. The base-stacking was a 3'-T (stabilizer oligo) abutting a 5'-A (reporter oligo), the weakest of all base-stacking interactions (R. Sinden, *DNA Structure and Function*, Academic Press, Inc. 1994). Moreover, the mismatch on the target DNA was a G, a nucleotide known to form weak bonds with an opposing A. The non-optimal discrimination achieved here could easily have been overcome by analyzing the opposite amplicon strand.

EXAMPLE II

Figure 3:
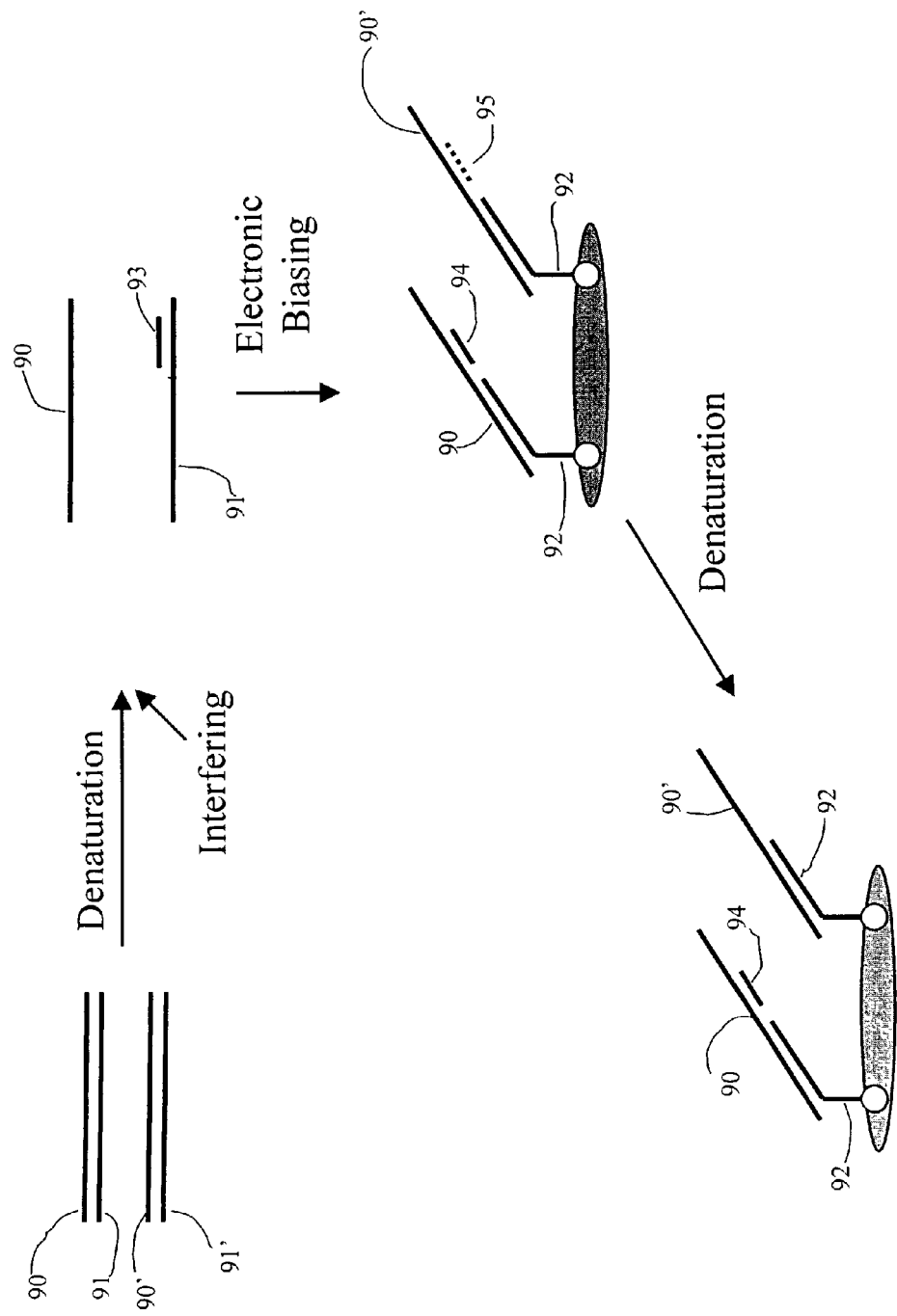
FIG. 3 is a representation of one embodiment of the method of electronic SNP scoring by dual fluorescent base-stacking format wherein the stabilizing probe is anchored to the capture site ("capture down" format). Additionally this figure demonstrates the use of interfering probes to compete out undesired amplicon strands. As is similarly demonstrated in FIG. 2, wild type and mutant alleles may be detected.

Besides the amplicon down format described in FIG. 2, a second format is useful wherein the stabilizer is anchored to specified capture sites (i.e., capture down format). As shown in FIG. 3, amplicon strands 90 and 91 may be denatured and combined with biotin labeled stabilizer oligo 92. Additionally, further enhancement of signal may be derived from the inclusion of an "interfering" oligomer 93 designed to be complementary to the undesired amplicon strand.

Following addressing of the hybridization complexes to capture sites, anchored stabilizer annealed to allelic strands of the target, 90 and 90' are probed with reporter oligos specific for wild type and mutant. In the figure, only one reporter is shown remaining following discrimination. Thus, as indicated in FIG. 3, the sample is homozygous for one allele.

This format has been successfully used for the detection of Hemochromatosis, Factor V, and EH1 mutations. In the preferred format, addressing of the amplicon occurs after denaturation. To prevent reannealing of the amplicon with its complementary strand at the capture site and to favor hybridization to the stabilizer probe, a specific interference oligonucleotide may be added to the protocol at the time of addressing to the capture site. This oligonucleotide is designed to be complementary to the undesired amplicon strand and should be present in molar excess. It should be designed to hybridize to the region outside of the stabilizer/reporter complementary region. In this way it will not interfere with hybridization of the stabilizer or reporter oligonucleotides to the desired amplicon. Rather, it will serve to "hold the amplicon open", inhibiting reannealing of the amplicon with its complement. The interference oligonucleotide may be placed 5' or 3' to the base-stacked complex site.

EXAMPLE III

FIG. 4 sets forth a format wherein multiple SNP containing reporter probes are used with one another to provide multiple base-stacking energies. FIG. 4a shows the capture down format while FIG. 4b shows the amplicon down format. In FIG. 4a, amplicon 42 is stabilized with stabilizer 41 that is anchored to a capture site via biotin moiety 40, and two reporter probes 43 and 44 are hybridized to detect the presence of at least two SNPs. FIG. 4b is similar except that the amplicon 45 is biotin labeled 4' and anchored to the capture site while stabilizer 46 is unlabeled.

This format is useful where there are multiple closely spaced SNPs at a single genetic locus. An example of this is the Mannose Binding Protein gene locus that correlates with susceptibility to sepsis in leukopenic patients. In this case there are 4 SNPs spaced within 15 bases of each other. Another example is the human HLA locus in which there are a large number of naturally occurring variants scattered within 3 exons. In this format, the reporter probes are base-stacked against a stabilizer oligo and each of the reporters may be labeled with a different fluorophore specific for an allele that occurs at these sites.

EXAMPLE IV

Figure 5:
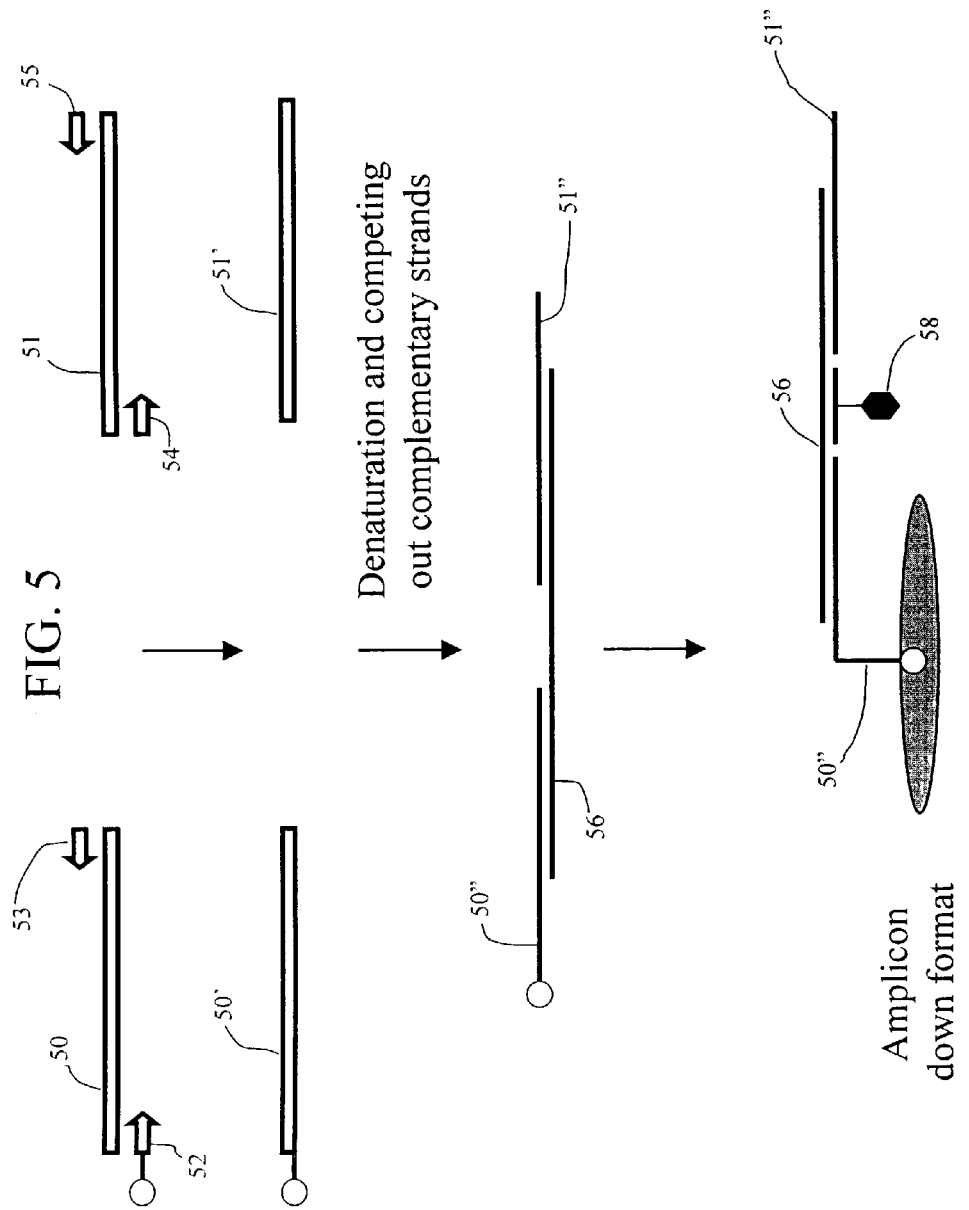
FIG. 5 represents one embodiment of the invention wherein base-stacking energies are provided by nesting a reporter probe between two target amplicons. In this example, the stabilizer probe has nucleic acid base sequence complementary to both target amplicons. The figure depicts amplicon down format although capture down is equally applicable. Stabilization of the reporter probe in nested fashion signals the presence of both target species and/or any SNP integrated into the 5' or 3' terminus, or into both termini, of the reporter probe.

FIG. 5 depicts a nested format wherein the target nucleic acid may be amplified using standard primers, one of which may be labeled (e.g., 52) for application of the amplicon down format. As shown, amplicons 50' and 51' may be denatured and mixed with stabilizer (and interfering oligo if desired) to yield stabilizer: amplicon hybridization complex (50"/56/51"). This complex is then addressed to a specified capture site followed by introduction of reporter probe 58 that benefits from base-stacking energies due to stabilizing interactions at both its 5' and 3' termini. Although only amplicon down format is illustrated, nested base-stacking can also be carried out using the capture down format.

This nested method is useful where there are multiple SNPs at a single genetic locus as described in EXAMPLE III as well as in situations where it is desired to detect SNPs from remote genetic loci. Moreover, this method is functional where it is desired to detect the presence of different and genetically unrelated amplicons whose coincident identification may provide useful information. Such information can be defined as "target-specific nucleic acid information" which provides some degree of identification of the nature of the target sequence. For example, a first region of a target nucleic acid may provide an amplicon used to identify the source of the nucleic acid (e.g., Staphylococcus vs. E. coli). The second amplicon may be used to identify a particular trait such as antibiotic resistance (e.g., methicillin resistance). The nesting of the reporter using base-stacking energies to stabilize its hybridization indicates that both amplicons are present in the sample.

The nesting reporter may provide additional data where SNPs are additionally associated with one or the other or both of the genetic loci from which the amplicons were generated. An example of this is the identification of bacteria by polymorphisms within a conserved gene sequence, such as 16S rDNA, or gyrase A sequences. In each one of these amplicons there may not be sufficient genetic divergence to uniquely identify all species or subspecies. Thus, use of a second independent locus can provide essential data. For example, gyrase A is useful alone however, discrimination between closely related bacterial strains may be greatly augmented by inclusion of polymorphisms in the gyrase B or par C loci.

A unique feature of the nested method is the reporter probe may incorporate SNP or other specific bases at both its 5' and 3' termini. Thus, internal bases of the reporter oligo can be designed to incorporate unique sequence complementary to internal base positions of the stabilizer, while the terminal bases of the reporter may comprise bases specific to stabilizer, SNPs, or other bases of the different genetic loci.

Figure 6:
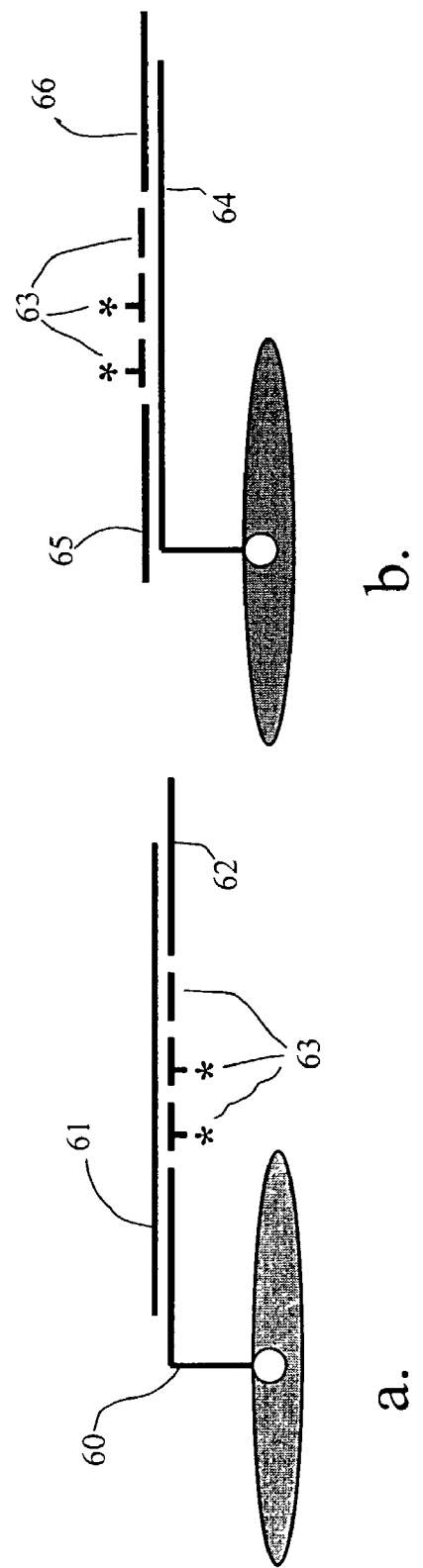
FIGS. 6a and b show that the nested embodiment illustrated in FIG. 5 may also utilize multiple base-stacking energies of multiple reporter probes, each of which may include SNPs. As with the other formats, both amplicon and capture down formats are useful.

FIG. 6 further depicts an additional aspect of the nested method wherein multiple reporters 63 may be nested to detect multiple SNPs that may be associated with either of the amplicon 60 and 62, or 65 and 66 species. As with single reporter nesting, both the amplicon down and the capture down formats are applicable.

Figure 7:
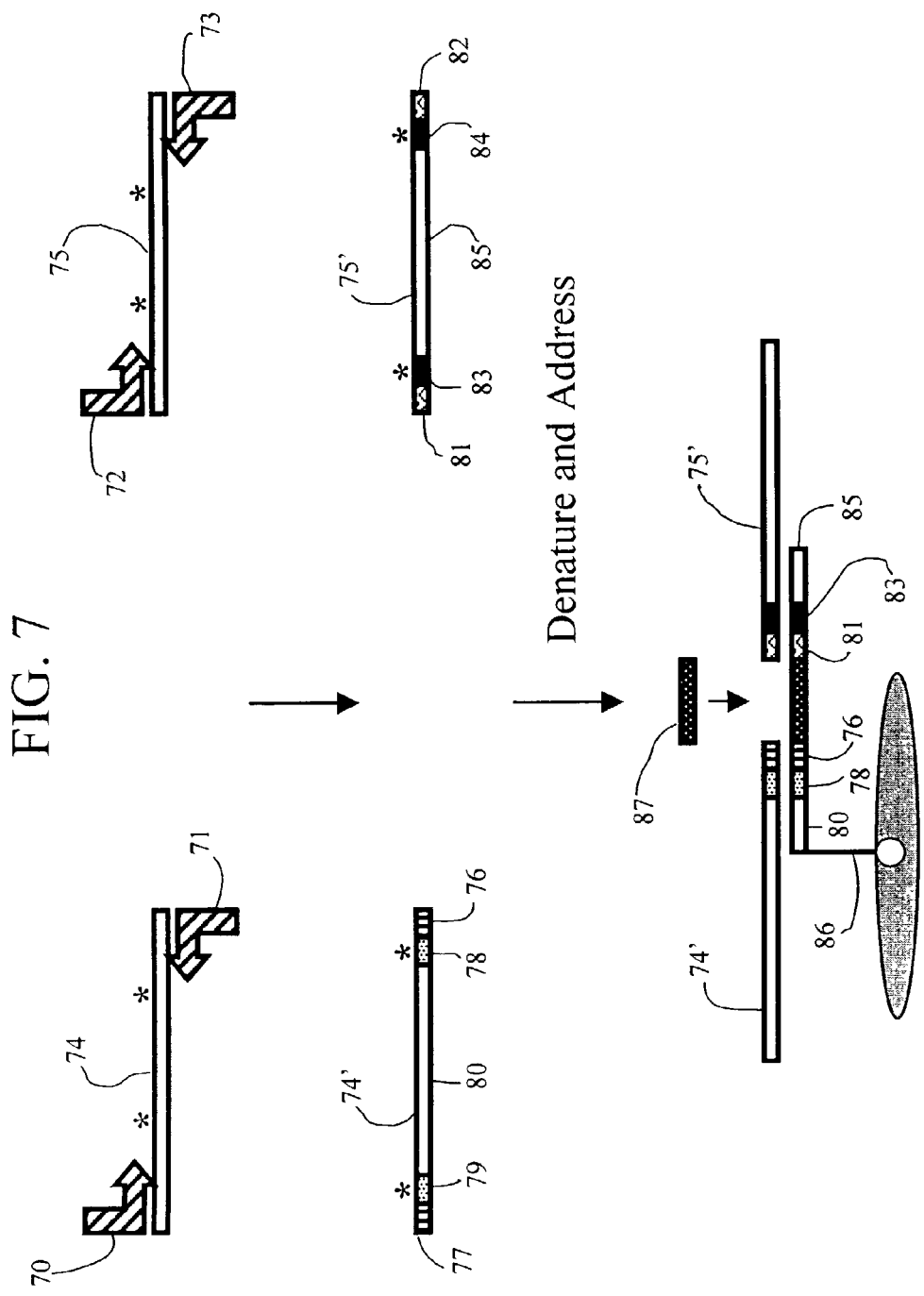
FIG. 7 shows a nested format in which amplification is carried out using SDA. In this embodiment, the termini of the amplicons necessarily possess sequence related to primers used in SDA that contain an endonuclease restriction site. In this embodiment, SNPs may be either in the reporter termini or alternatively be in amplicon sequence immediately internal to the SDA primer sequence. In either case, mismatches can be detected by destabilizing hybridization of the reporter probe due to mismatches on the reporter itself or mismatches in the amplicon sequence. Additionally, amplicons generated using SDA may use either amplicon or capture down format (capture down shown) and may use multiple reporter stacking.

FIG. 7 further depicts a variation of the nested method wherein amplification of the target is carried out using SDA. In this situation, because the amplification primers incorporate nucleic acid sequence related to the amplification process (i.e., restriction endonuclease sequence), the termini of the amplicons hybridized to the stabilizer do not represent target-specific sequence. This creates the necessity for the stabilizer oligo to be designed such that SDA primer sequence abut a nesting reporter probe. Specifically, primers 70 and 71 specific for target locus 74, and primers 72 and 73 for target locus 75, each contain necessary restriction sites (e.g., Bso B1). Upon amplification, amplicons 74' and 75' are flanked by primer sequences 76, 77, and 81, 82 respectively. Internal to theses flanking sequences may be located the specific SNP containing sequences of interest 78,79, 83, and 84, which in turn flank target specific sequence 80 and 85. This arrangement requires that the stabilizer oligo be designed to incorporate each of the above sequences in order to hybridize both amplicons and stabilizer into a complex. This additionally means that the stabilizer incorporates SNP sensitive sequence rather than the reporter oligo. Although capture down format is depicted, the amplicon format is equally applicable.

Following anchoring of the complex, reporter probe 87 is hybridized to the complex in a nested fashion. In this situation, the reporter may be designed to be stabilized where there is not any mismatches between the stabilizer and amplicon. In contrast, if mismatches were present, hybridization between the stabilizer and amplicon would necessarily result in a "bubble" formation allowing such mismatches to provide the destabilization necessary to keep the reporter from hybridizing.

In each of the above examples, base-stacking schemes are provided that achieve discrimination by breaking long regions of hybridization into two or more sequences. This methodology allows for discrimination of specific nucleic acid sequences from relatively short probes. The fact that short probes are used provides the opportunity to use detection mechanisms sensitive to both passive and electronic hybridization techniques. Moreover, the use of short probes provides the opportunity to use detection mechanisms based solely on the probe's mass (i.e., mass spectrometry) where extremely high levels of mass resolution are achieved by direct measurement (e.g. by flight or ESI). In such case, reporter probes having a length of 50 bases or less are preferred. Detection using mass spectrometry could be carried out by separating the probe from the hybridization complex and launching it directly to the mass spec detector.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

We claim:

1. A method for detecting a single nucleotide polymorphism in a sample nucleic acid using an electronically addressable microchip having a plurality of test sites, wherein each of the test sites comprises an individually controllable electrode covered by a permeation layer, the method comprising:

providing a sample nucleic acid suspected of containing a single nucleotide polymorphism;

electronically biasing the sample nucleic acid to a test site of the plurality of test sites on the microchip, and concentrating the sample nucleic acid at the test site;

immobilizing the sample nucleic acid onto the test site;

electronically hybridizing a mixture comprising a first probe with a label selected from the group consisting of fluorescent label, colorimetric label, and chemiluminescent label, and a second probe with a label selected from the group consisting of fluorescent label, colorimetric label, and chemiluminescent label to the sample nucleic acid, wherein the first probe is perfectly complementary to the sample nucleic acid and contains a nucleotide perfectly complementary to the nucleotide at the site of the polymorphism, and forms a first hybridized complex, and the second probe is complementary to the sample nucleic acid and contains a nucleotide which forms a mismatch with the nucleotide at the site of the polymorphism, and forms a second hybridized complex, wherein the label of the first probe and the label of the second probe are different;

subjecting the first and second hybridized complexes to destabilizing conditions sufficient to cause the first probe to dissociate from the first hybridized complex or the second probe to dissociate from the second hybridized complex if there is at least one base-pair mismatch between the first probe or the second probe and the sample nucleic acid; and detecting the first or second hybridized complex following the subjecting step by determining a signal intensity from the label of the first probe of the first hybridized complex or a signal intensity from the label of the second probe of the second hybridized complex, wherein the single nucleotide polymorphism in the sample nucleic acid is detected if the signal intensity from the label of the first probe of the first hybridized complex is present.

2. The method of claim 1, further comprising the step of subjecting the sample nucleic acid to an amplification reaction before said biasing step.

3. The method of claim 1, wherein the sample nucleic acid further comprises a biotin moiety, and wherein the sample nucleic acid is immobilized onto the test site by a biotin-streptavidin interaction.

4. The method of claim 1, wherein the label of the first probe and the label of the second probe are different fluorophores.

5. The method of claim 4, wherein the different fluorophores are selected from the group consisting of Cy3 and Cy5.

6. The method of claim 1, further comprising the steps of:

providing another sample nucleic acid containing the single nucleotide polymorphism;

electronically biasing the another sample nucleic acid to an another test site of the plurality of test sites on the microchip, concentrating the another sample nucleic acid at the another test site; and immobilizing the another sample nucleic acid onto the another test site.

7. The method of claim 1, wherein the hybridization step is repeated with at least one additional mixture of the first and second probes.

8. The method of claim 1, wherein the hybridization step is performed under electronic stringency conditions.

* * * * *